US012751749B2

(12) United States Patent
Gault et al.

(10) Patent No.: US 12,751,749 B2
(45) **Date of Patent: *Oct. 6, 2026**

(54) SYSTEM FOR JOINT FIXATION OF EXTREMITY BONE AND RELATED METHODS

(71) Applicant: Forma Medical, Inc., Camp Hill, PA (US)

(72) Inventors: James A. Gault, Lincoln, RI (US); Andrew Charles Davison, Hummelstown, PA (US); Christopher F. Hyer, Worthington, OH (US); Jesse F. Doty, Hixson, TN (US); A. Holly Johnson, New York, NY (US)

(73) Assignee: Forma Medical, Inc., Camp Hill, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/532,626

(22) Filed: Feb. 6, 2026

(65) Prior Publication Data

US 2026/0165758 A1 Jun. 18, 2026

Related U.S. Application Data

(63) Continuation of application No. 19/203,592, filed on May 9, 2025, which is a continuation of application (Continued)

(51) Int. Cl.
*A61B 17/80* (2006.01)
*A61B 17/17* (2006.01)

(Continued)

(52) U.S. Cl.
CPC ........ *A61B 17/808* (2013.01); *A61B 17/1728* (2013.01); *A61B 17/846* (2013.01); *A61F 2/4225* (2013.01); *A61B 17/1739* (2013.01); *A61B 17/1775* (2016.11); *A61B 17/56* (2013.01); *A61B 2017/564* (2013.01);

(Continued)

(58) Field of Classification Search
CPC . A61B 17/808; A61B 17/1728; A61B 17/846; A61B 17/80; A61B 17/8004; A61B 17/8014; A61B 17/8052; A61B 2017/8655; A61B 2017/564; A61B 2017/568; A61F 2/4225; A61F 2/42; A61F 2/4202;

(Continued)

(56) References Cited

U.S. PATENT DOCUMENTS 12,521,157 B1 * 1/2026 Gault ................ A61B 17/8061
2012/0065689 A1 3/2012 Prasad et al.

(Continued)

OTHER PUBLICATIONS

Hsu, A R. (Jul. 8, 2016). Joint Prep, compression, rigid fixation among keys to hallux MTP joint arthrodesis. Healio. https://www.healio.com/news/orthopedics/20160708/joint-prep-compression-rigid-fixation-among-keys-to-hallux-mtp-joint-arthrodesis (Year: 2016).

(Continued)

*Primary Examiner* — Marcela I. Shirsat
(74) *Attorney, Agent, or Firm* — Offit Kurman; Gregory A. Grissett; Chad Sayala

(57) ABSTRACT

A bone fixation system configured to fix one or more bone segments of extremity bones is provided.

27 Claims, 38 Drawing Sheets

Related U.S. Application Data

No. 19/078,434, filed on Mar. 13, 2025, now Pat. No. 12,521,157.

(60) Provisional application No. 63/670,414, filed on Jul. 12, 2024.

(51) Int. Cl.

| | |
|---|---|
| ***A61B 17/56*** | (2006.01) |
| ***A61B 17/58*** | (2006.01) |
| ***A61B 17/84*** | (2006.01) |
| ***A61B 17/86*** | (2006.01) |
| ***A61B 17/88*** | (2006.01) |
| ***A61B 17/90*** | (2006.01) |
| ***A61F 2/42*** | (2006.01) |

(52) U.S. Cl.

CPC ........... *A61B 17/58* (2013.01); *A61B 17/8004* (2013.01); *A61B 17/8014* (2013.01); *A61B 17/8052* (2013.01); *A61B 17/8057* (2013.01); *A61B 17/8061* (2013.01); *A61B 2017/8655* (2013.01); *A61B 17/8872* (2013.01); *A61B 17/90* (2021.08); *A61F 2002/4228* (2013.01); *A61F 2002/4233* (2013.01); *A61F 2002/4238* (2013.01)

(58) Field of Classification Search

CPC ...... A61F 2002/4228; A61F 2002/4233; A61F 2002/4238

USPC .......................................................... 606/286

See application file for complete search history.

(56) References Cited

U.S. PATENT DOCUMENTS

| | | | |
|---|---|---|---|
| 2014/0081341 | A1 | 3/2014 | Chun-Li et al. |
| 2014/0277176 | A1 | 9/2014 | Buchanan et al. |
| 2016/0213384 | A1 | 7/2016 | Fallin et al. |
| 2017/0049576 | A1 | 2/2017 | Guilford et al. |
| 2019/0110818 | A1 | 4/2019 | Grant |
| 2019/0358039 | A1 | 11/2019 | Ducharme et al. |
| 2021/0236180 | A1 | 8/2021 | DeCarbo et al. |
| 2022/0183733 | A1 | 6/2022 | Coale et al. |
| 2022/0226029 | A1 | 7/2022 | Heavener et al. |
| 2024/0108364 | A1 | 4/2024 | Penner et al. |
| 2025/0017604 | A1 | 1/2025 | Dewey et al. |

OTHER PUBLICATIONS

European Patent Office, "PCT International Search Report and Written Opinion of the International Searching Authority," Jun. 5, 2025 (18 pages), Netherlands.

* cited by examiner

SYSTEM FOR JOINT FIXATION OF EXTREMITY BONE AND RELATED METHODS

CROSS-REFERENCE TO RELATED APPLICATIONS

The present application is a continuation of U.S. application Ser. No. 19/203,592, filed May 9, 2025, which is a continuation of U.S. application Ser. No. 19/078,434, filed Mar. 13, 2025, issued as U.S. Pat. No. 12,521,157, all of which claim the benefit of and priority to U.S. Provisional Application No. 63/670,414, filed Jul. 12, 2024, the entire disclosures of which are incorporated by reference into this application.

TECHNICAL FIELD

The present disclosure relates generally to a system for joint fixation of extremity bones and related methods.

BACKGROUND

A common procedure for handling healing of broken bones and addressing deformities such as hammertoe or arthritis is the use of bone fixation implants for fusing one or more adjacent bones. Conventional bone fixation implants utilize generic screws and wires that create a rigidly fused joint with very limited adjustability intraoperatively. Some implants offer some limited degree of flexibility and/or adjustment when used under very specific circumstances that require highly technical surgical procedures. Such existing bone fixation implants often require multiple components with many intricate mating features requiring customization depending on the type of bone, patient, or desired location of the implant in the body of a patient. This results in increased costs, less desirable healing outcomes, and multiple procedures to achieve a desired outcome.

SUMMARY

Thus, there is still a need for a bone fixation system and related surgical instruments capable of being implanted that addresses the problems of conventional bone fixation implants including providing flexibility in bone-to-bone alignment and fusion with less invasive procedures that are pragmatic for the operating room and applicable for use with some of the smallest bones of the human anatomy.

An embodiment of the present disclosure includes a system for fixation or fusion of bone segments in an extremity bone. The system also includes a bone plate having one or more proximal through-holes and one or more distal through-holes spaced apart from the one or more proximal through-holes, where the bone plate is configured so that when the bone plate is implanted across a first and second bone segments, the one or more proximal through-holes are positioned adjacent the first bone segment and the one or more distal through-holes are positioned on the second bone segment. The system also includes one or more proximal bone anchors configured to be inserted into the one or more proximal through-holes of the bone plate into the first bone segment when the bone plate is in positioned adjacent the extremity bone. The system also includes one or more distal bone anchors configured to be inserted into the one or more distal through-holes of the bone plate when the bone plate is in positioned adjacent the extremity bone. The system also includes a crossing anchor having a shaft with a proximal end and a distal end spaced from the proximal end along a central axis, a proximal end having a proximal beveled surface that is angled with respect to the central axis to sit substantially flush with a bone surface when implanted in one or both of the first and second bone segments. The system also includes where the crossing anchor is configured to span the first and second bone segments and be spaced from the bone plate, the shafts of the one or more proximal and the shaft of the one or more distal bone anchors when the bone plate and the one or more proximal bone anchors and the one or more distal bone anchors are implanted into the respective bone segments of the extremity bone.

Another embodiment includes a method that includes forming a first incision in tissue near a first bone segment. The method also includes coupling one or more drill guides to a bone plate at one or more through-holes at a trailing end of the bone plate. The method also includes inserting a leading end of the bone plate into the first incision toward a second bone segment with the one or more drill guides coupled to the trailing end of the bone plate. The method also includes positioning the bone plate in the first incision so that the bone plate spans the first bone segment and the second bone segment. The method also includes forming a second incision near the where the leading end is located near the second bone segment. The method also includes implanting one or more first bone anchors into one or more through-holes at the trailing end of the bone plate and into the first bone segment. The method also includes implanting one or more second bone anchors through the second incision into one or more through-holes at the leading end of the bone plate into the second bone segment.

Another embodiment includes a method that includes forming an incision near a foot bone. The method also includes inserting a leading end of a bone plate into the incision and under an extensor hallucis longus (EHL) tendon and above the foot bone until the leading end is located adjacent a first bone segment of the foot bone, where the leading end includes one or more through-holes. The method also includes positioning the bone plate across the first bone segment and a second bone segment of the foot bone so that a central bridge of the bone plate is underneath the EHL tendon, the leading end is located one on side of the EHL tendon, and a trailing end of the bone plate is located on the other side of the EHL tendon of the foot bone. The method also includes implanting one or more first bone anchors into one or more through-holes at the leading end of the bone plate and into the first bone segment of the foot bone. The method also includes implanting one or more second bone anchors into the one or more through-holes of the trailing end of the bone plate and into the second bone segment of the foot bone.

Another embodiment includes a method that also includes forming a first incision near a foot bone. The method also includes inserting a leading end of a bone plate into the incision, where the leading end includes one or more through-holes. The method also includes positioning the bone plate across the foot bone so that a central bridge of the bone plate spans a first metatarsal and a first cuneiform bone, the leading end is located on one of the first metatarsal and the first cuneiform bone, and a trailing end of the bone plate is located on the other of the first metatarsal and the first cuneiform bone. The method also includes forming a second incision in tissue near the where the leading end is located. The method also includes implanting one or more first bone anchors into one or more through-holes at the trailing end of the bone plate into one of the first metatarsal and the first cuneiform bone. The method also includes implanting one implanting one or more second bone anchors through the second incision and into one or more through-holes at the leading end of the bone plate into the other of the first metatarsal and the first cuneiform bone.

Another embodiment includes a system for fixation or fusion of bone segments in an extremity bone. The system also includes a targeting instrument having a platform, a guide body having one or more guide channels, a stabilizing guide channel for receiving a stabilizing wire, where the one or more guide channels have a size and shape configured to receive one or more drill guides.

Another embodiment includes an anchor targeter having a base sized and shaped rotatably engage the platform, an aiming arm extending and curving from the base, an aiming body at a terminal end of the arm, and an aiming channel that extends through the aiming body, the aiming channel extending along a targeting axis that is inferior to and does not intersect the platform, where the anchor targeter is configured to rotate relative to the platform to align the targeting axis with a desired anchor trajectory.

BRIEF DESCRIPTION OF THE DRAWINGS

The foregoing summary, as well as the following detailed description of exemplary embodiments of the present application, are better understood when read in conjunction with the appended drawings. For the purposes of illustrating the present application, there is shown in the drawings, exemplary embodiments of the disclosure. It should be understood, however, that the application is not limited to the precise arrangements and instrumentalities shown. In the drawings.

DETAILED DESCRIPTION OF ILLUSTRATIVE EMBODIMENTS

Figure 1:
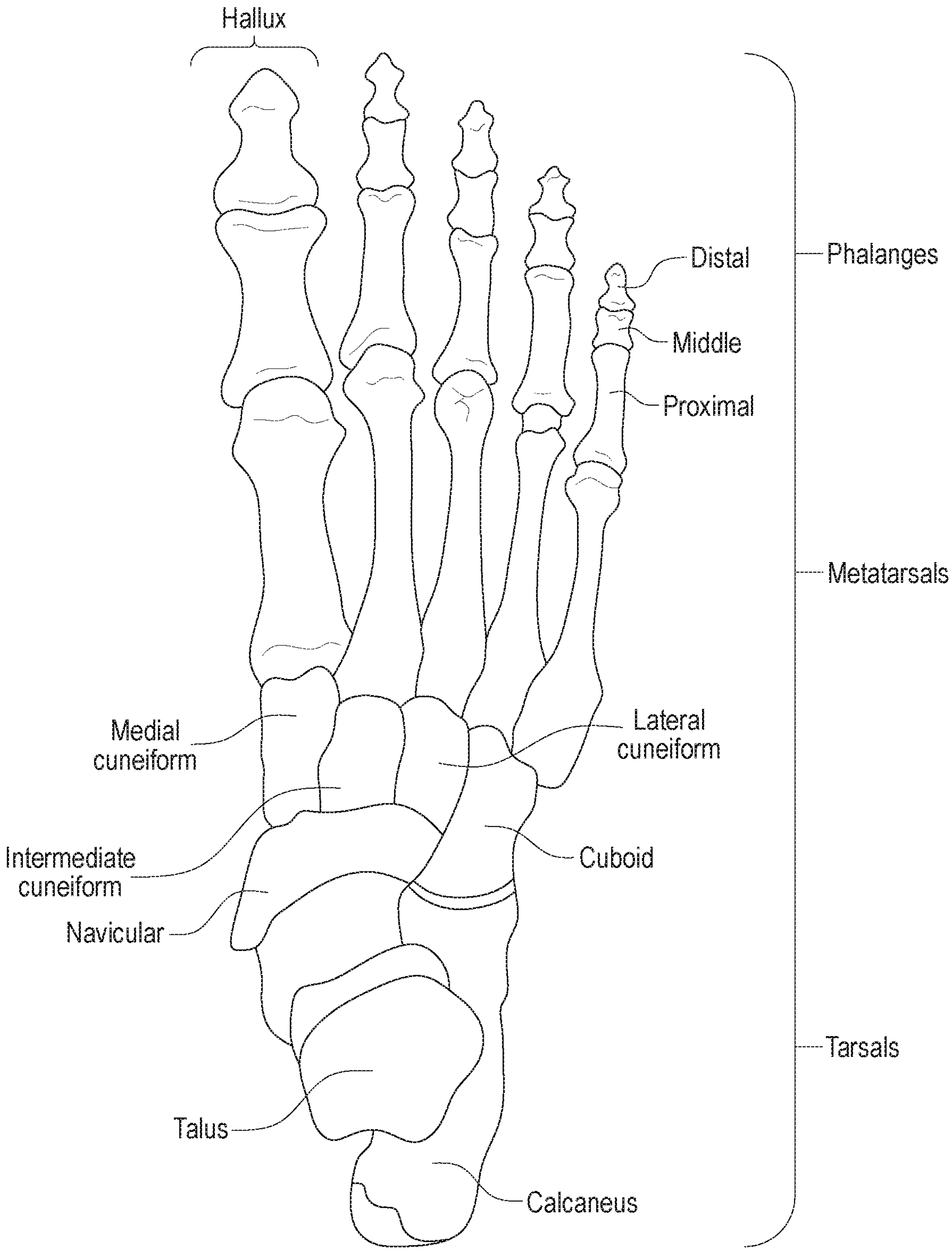
FIG. 1 is a top view of an anatomical foot.
Figure 2:
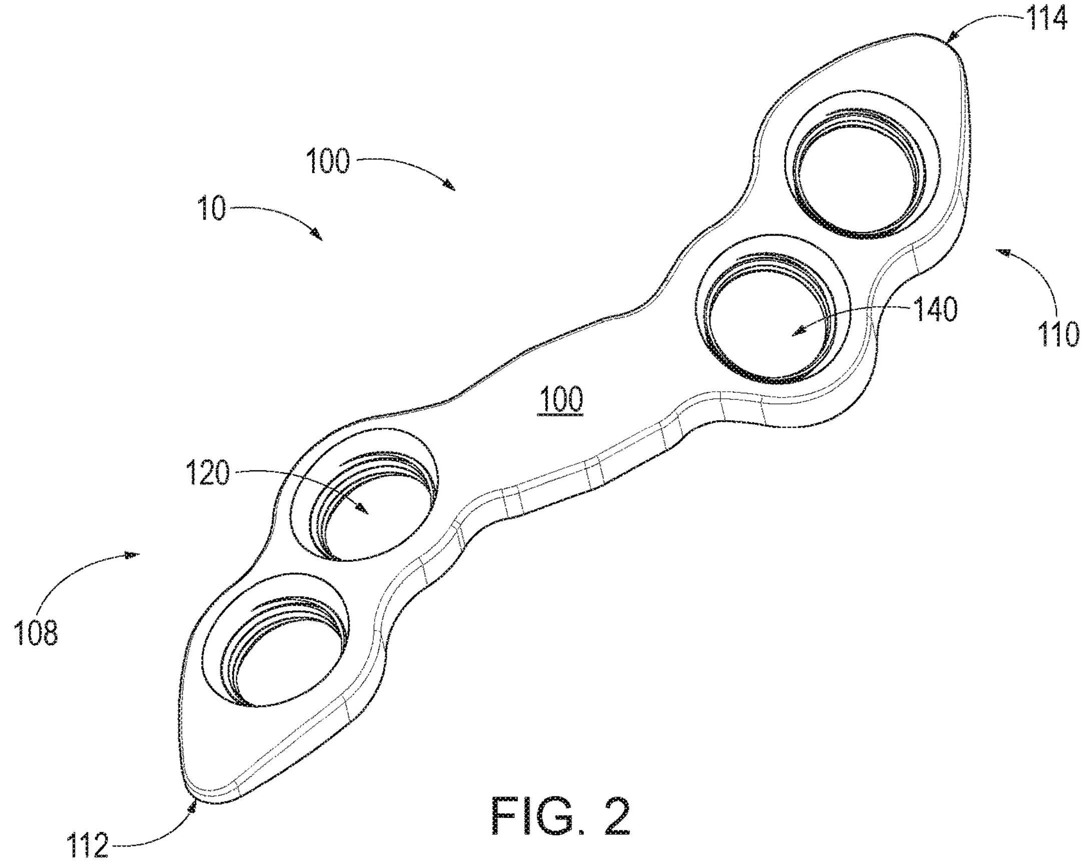
FIG. 2 is a top perspective view of a bone plate of a bone fixation system according to an embodiment of the present disclosure.
Figure 3:
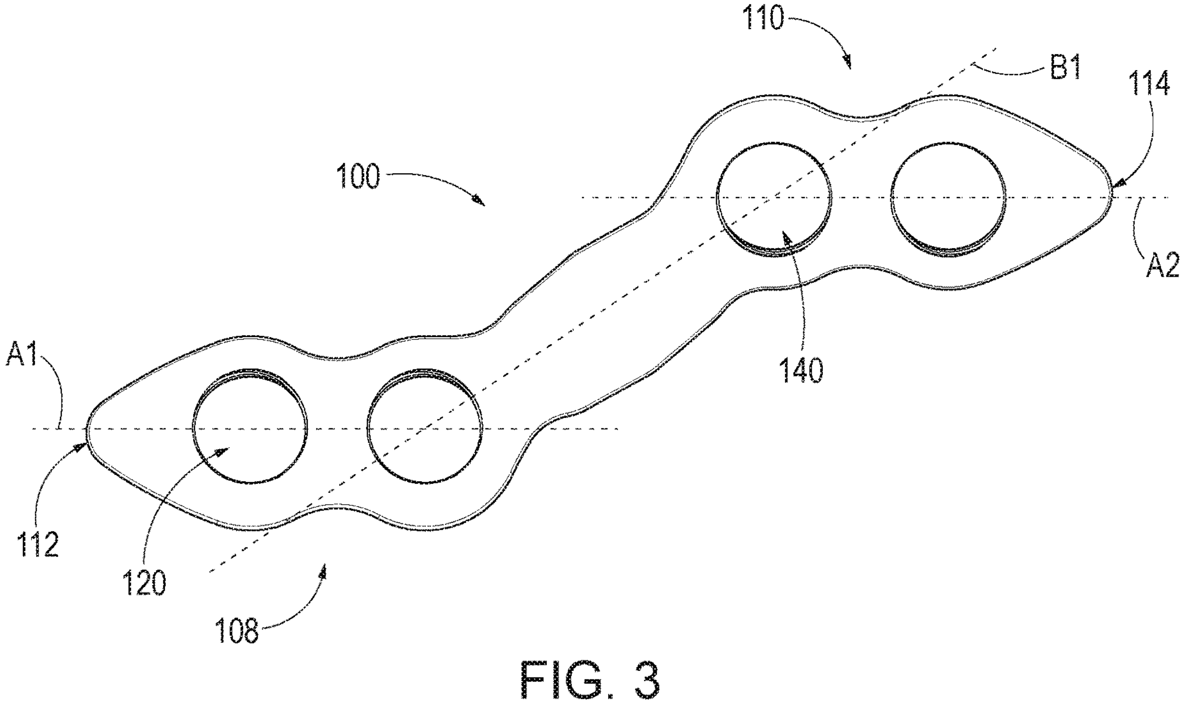
FIG. 3 is a bottom view of the bone plate shown in FIG. 2.
Figure 4:
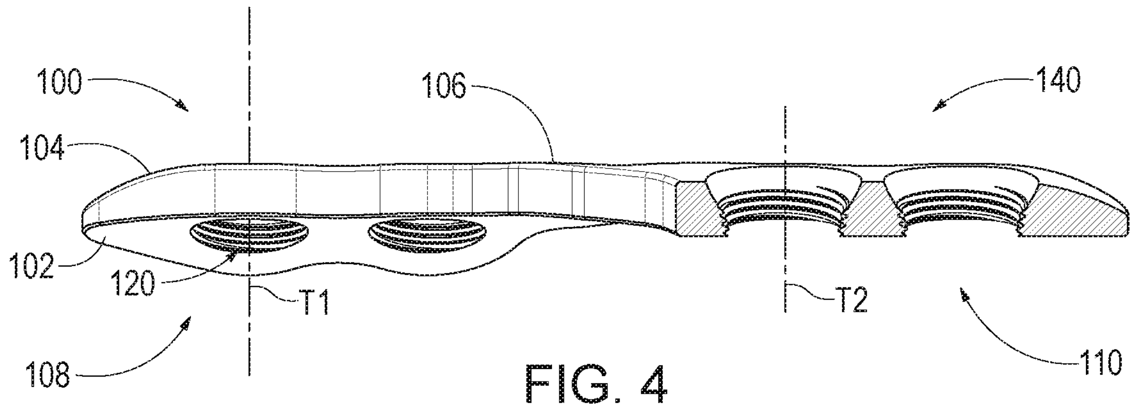
FIG. 4 is a side cross-sectional view of a portion of the bone plate shown in FIGS. 2-3.
Figure 5:
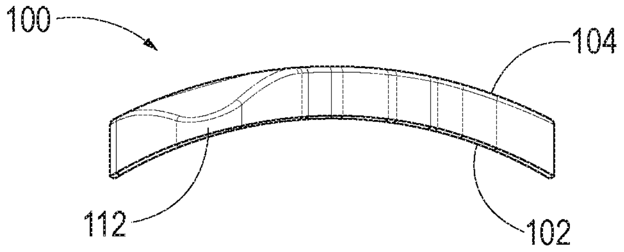
FIG. 5 is an end view of the bone plate shown in FIGS. 2-4.

Bone fixation devices as described are configured for aid in the fixation of two or more bones or bone segments, typically in extremity bones, such as the foot. As shown in FIG. 1, the skeletal anatomy of a foot includes tarsals, metatarsals, and phalanges. The foot bone structure is further typically divided into three regions: the hindfoot, midfoot, and forefoot. The tarsal bones are seven bones in the hindfoot and midfoot and include the calcaneus, talus, cuboid, navicular, and three cuneiforms. The metatarsal bones are five bones in the forefoot that connect the tarsals to the phalanges. The phalanges in the forefoot that form the toes. The systems and methods as described herein are used for fusion procedures in the foot, however, the systems and procedure can be used for other extremity bones as needed.

The bone fixation systems and devices as described herein are configured for fixation of bone structure in the foot. More specifically, the systems and method described here are configured for metatarsal phalangeal (MTP) fusion of the big toe, such as for example to treat pain from arthritis. The system and method described herein could be used for tarsometarsol (midfoot) fusion. In addition, the system and methods described herein could be used in a so-called Lapidus procedure, which is a surgical procedure used to treat a bunion deformity, also known as hallux valgus, which involves fusing the joint between the first metatarsal bone and one of the small bones in the medial cuneiform. In other examples, the bone fixation system and devices are configured for interphalangeal joint fixation. For example, the bone fixation devices may be used for fixation of metatarsals, proximal phalanges, middle phalanges, or distal phalanges. While the embodiments described are configured for interphalangeal joint fixation, it is possible that the described embodiments could be configured for fixation of phalanges, metatarsals, cuneiform, or cuboid bones in the foot. In other embodiments, the bone fixation devices may be configured for fixation of bone segments of phalanges, metatarsals or other bones in the hand.

Figure 27:
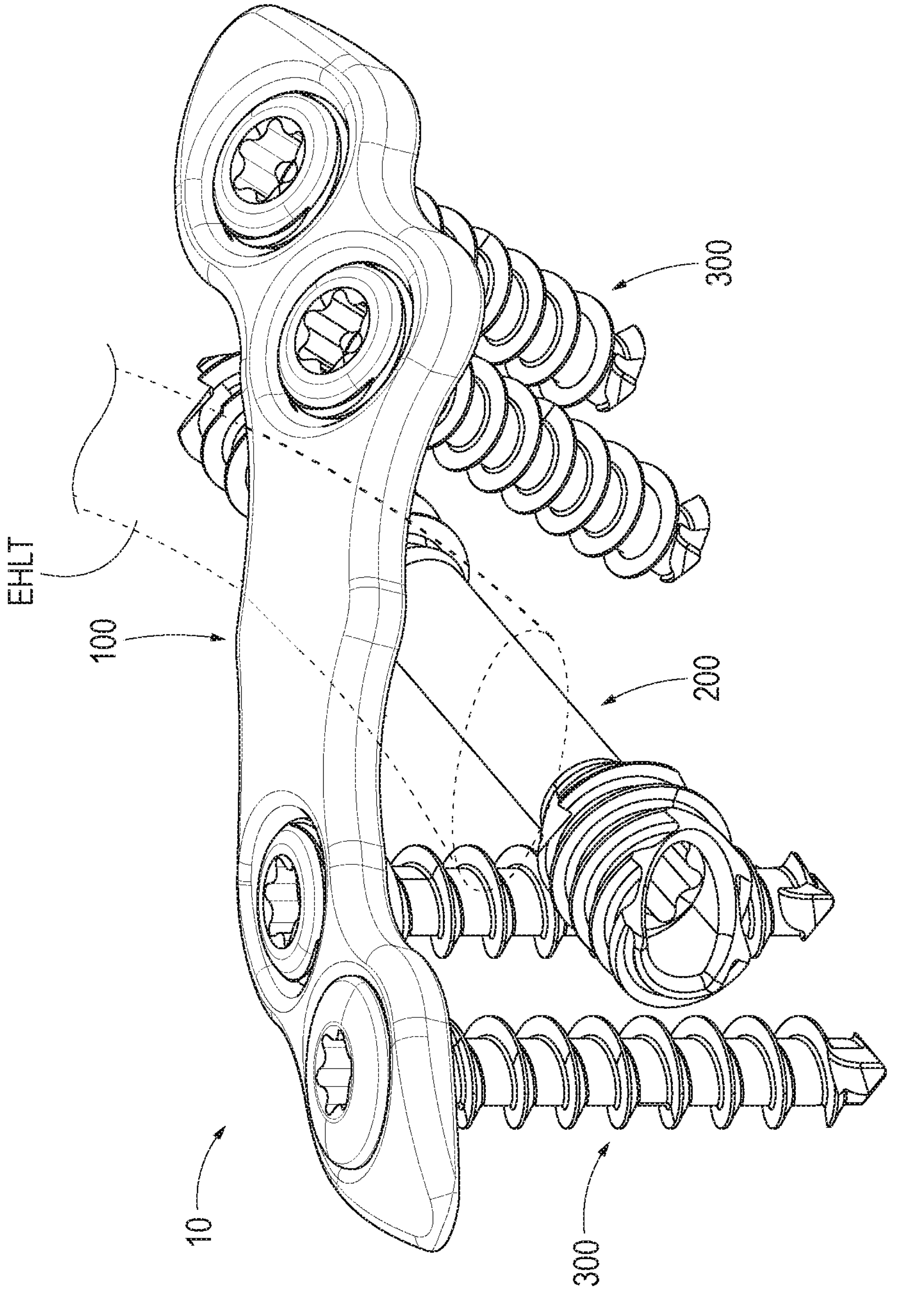
FIG. 27 illustrates top perspective view a bone plate, bone anchors, and crossing anchors in an implanted state with the bone removed for illustrative purposes.
Figure 28:
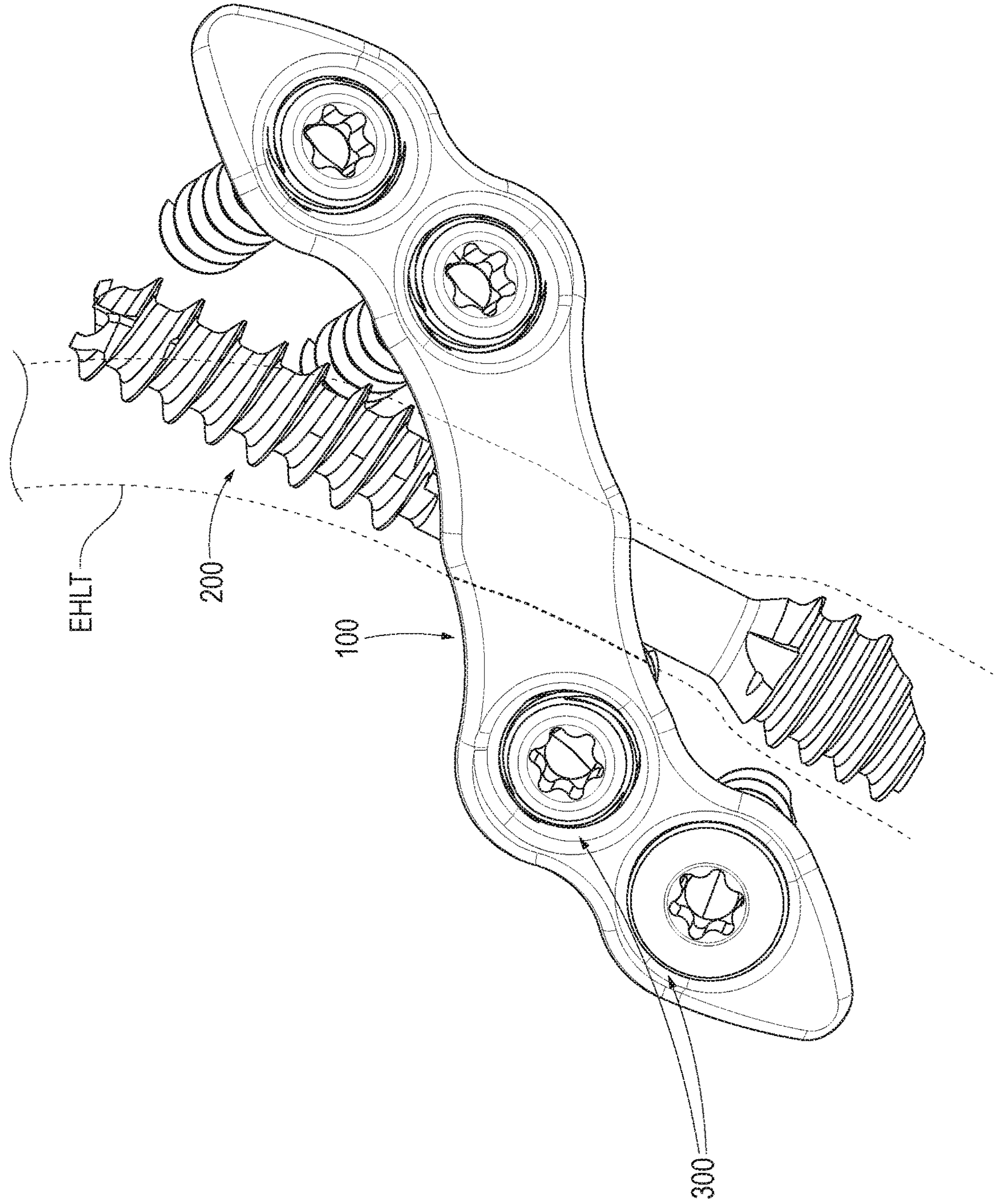
FIG. 28 illustrates a top view of the bone plate, bone anchors, and crossing anchors in an implanted state with the bone removed for illustrative purposes.
Figure 29:
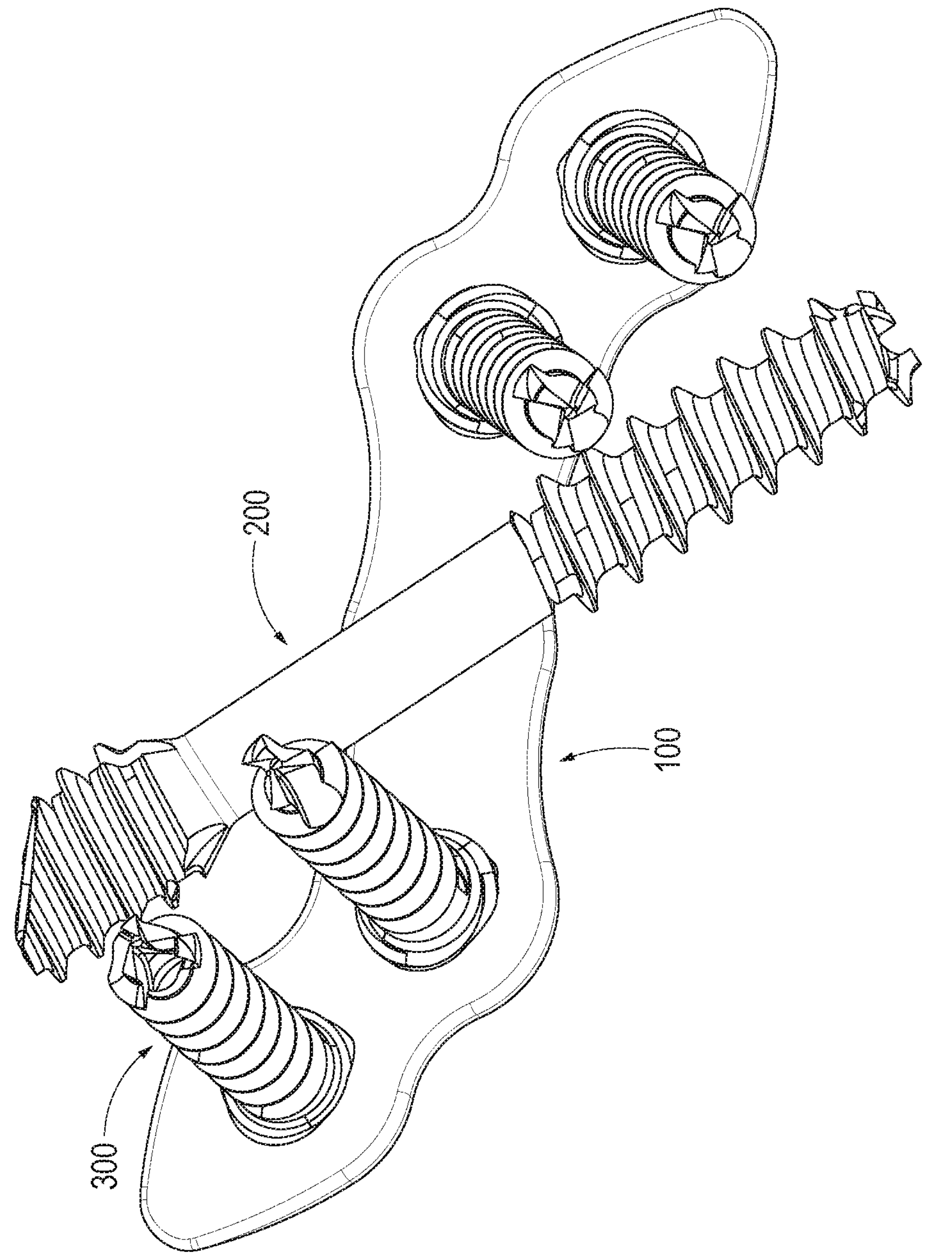
FIG. 29 illustrates a bottom view of the bone plate, bone anchors, and crossing anchors in an implanted state with the bone removed for illustrative purposes.
Figure 30:
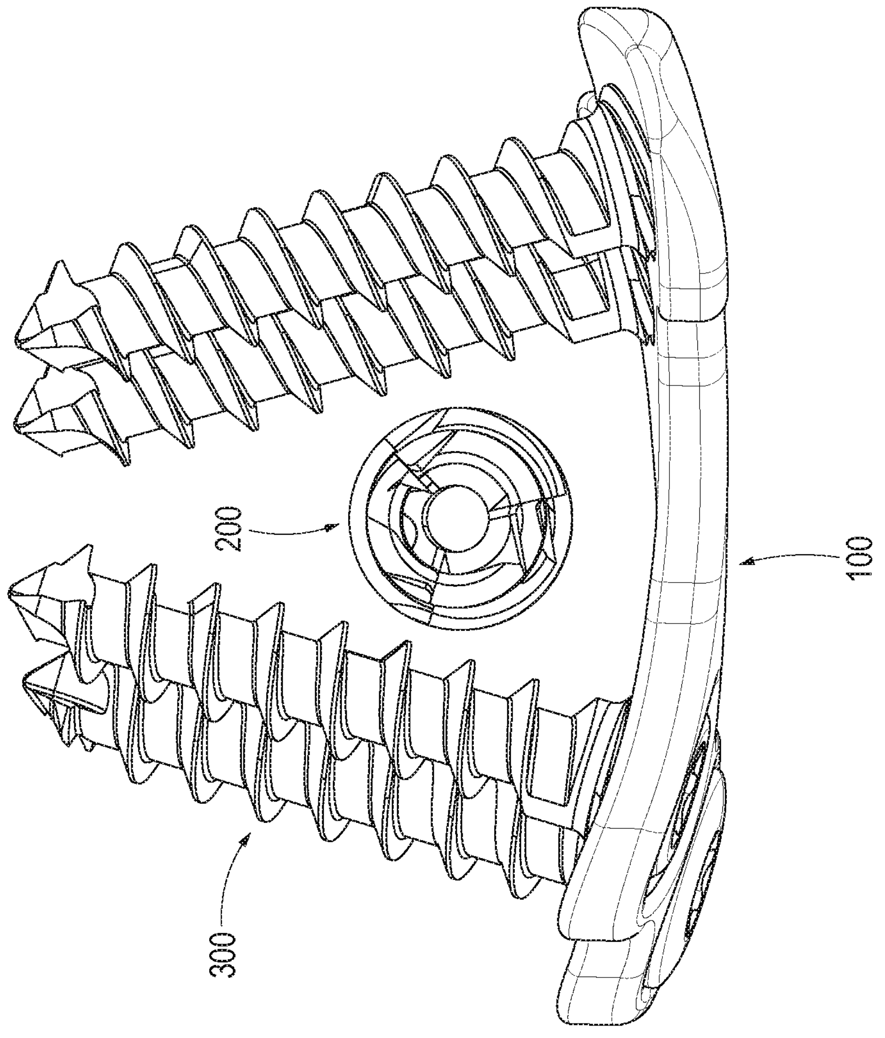
FIG. 30 illustrates an end view of the bone plate, bone anchors, and crossing anchors in an implanted state with the bone removed for illustrative purposes.

Referring to FIGS. 2-8, there is shown an exemplary embodiment of a bone fixation system 10 (FIG. 27) configured to configured to join bones or bone segments together. The bone fixation system 10 includes a bone plate 100, a crossing anchor 200, a set of bone anchors 300, 350.

The bone fixation system 10 may also a targeting instrument 400 (FIGS. 10-11) and an anchor targeter 500 (FIG. 12) connectable to the targeting instrument 400. One or more drill guides 550 may be used to aid in placement of the bone plate 100 relative to the targeting instruments 400, 500 during use. Other devices, such as fixation wires, k-wires, fixation pins and the like may be used to aid in the targeting and delivery of the bone anchors relative to the bone plate 100. Drivers and the like may be used during the procedure as will be further described below.

Referring to FIGS. 2-6, a bone plate 100 has an inferior surface 102, a superior surface 104 opposite the inferior surface 102. The inferior surface of the bone plate 100 is curved to conform to the anatomy of the foot bone against which it is placed. The superior surface 104 may track the same or substantially similar curvature of the inferior surface 102.

The bone plate 100 includes a central portion (or central bridge 106) configured to span a joint, a proximal fixation portion 108 extending from and angularly offset with respect to the central bridge 106, and a distal fixation portion 110 extending from and angularly offset with respect to the central bridge 106. The central bridge 106 extends along a bridge axis B1.

The bone plate 100 may have a proximal end 112 at the proximal fixation portion 108 that is tapered, and a distal end 114 at the distal fixation portion 110 that is tapered. The tapered proximal and distal ends 112, 114 are configured to guide the bone plate 100 between skin and bone proximate and across joint during insertion to the fixation site. The proximal end may be referred to a leading end of the bone plate and the distal end may be referred to as the trailing end of the bone plate, depending on direction of insertion. Likewise, the proximal end of the bone plate may be referred to as the trailing end of the bone plate and the distal end of the bone plate may be referred to as the leading end of the bone plate. Thus, the two opposed ends may be referred to a proximal, distal, trailing, or leading based on context.

The proximal fixation portion 108 has one or more through-holes 120 that extend from the superior surface 104 to the inferior surface 102. In the embodiment shown, the proximal fixation portion has first and second through-holes 120, which include partially threaded inner walls. Thus, the first and second through-holes 120 can receive either locking bone anchors or compression anchors. The through-holes 120 of the proximal fixation portion 108 extends along a through-hole axis T1 and include an upper portion that is tapered inward toward the through-hole axis T1. As shown in the figures, the one or more through-holes 120 are generally aligned along a first axis A1.

The distal fixation portion 110 has one or more through-holes 140 that extend from the superior surface 104 to the inferior surface 102. The distal fixation portion 110 has first and second through-holes 140, which include partially threaded inner walls as shown. Thus, the first and second through-holes 140 can also receive either locking bone anchors or compression anchors. The through-holes 140 of the distal fixation portion 110 extends along a through-hole axis T2 and include an upper portion that is tapered inward toward the through-hole axis T2. In the example shown, while the proximal fixation portion 108 and distal fixation portion 110 each include two through-holes, more or less through-holes may be used in each portion of the bone plate 100. The one or more distal through-holes 140 are aligned along a second axis A2.

The bone plate 100 may include sets of bores (not shown) for receiving wires, such as a k-wires or fixation pines. These bores may be placed between two adjacent through-holes and/or between a through-hole and the proximal and distal ends of the plate, respectively.

The central bridge 106 offsets the through-holes 120, 140 in proximal and distal fixation portions of the bone plate 100 such that the first axis A1 and the second axis A2 do not intersect. For example, the first axis A1 and the second axis A2 may be parallel. Furthermore, the central bridge 106 extends along the bridge axis B1 and forms oblique angles with the first axis A1 and the second axis A2. These configurations result in a bone plate that can span a fixation site and allow fixation with bone anchors so that the anchors fall on either side of the extensor hallucis longus (EHL) tendon when the bone plate 100 is implanted.

Figure 6:
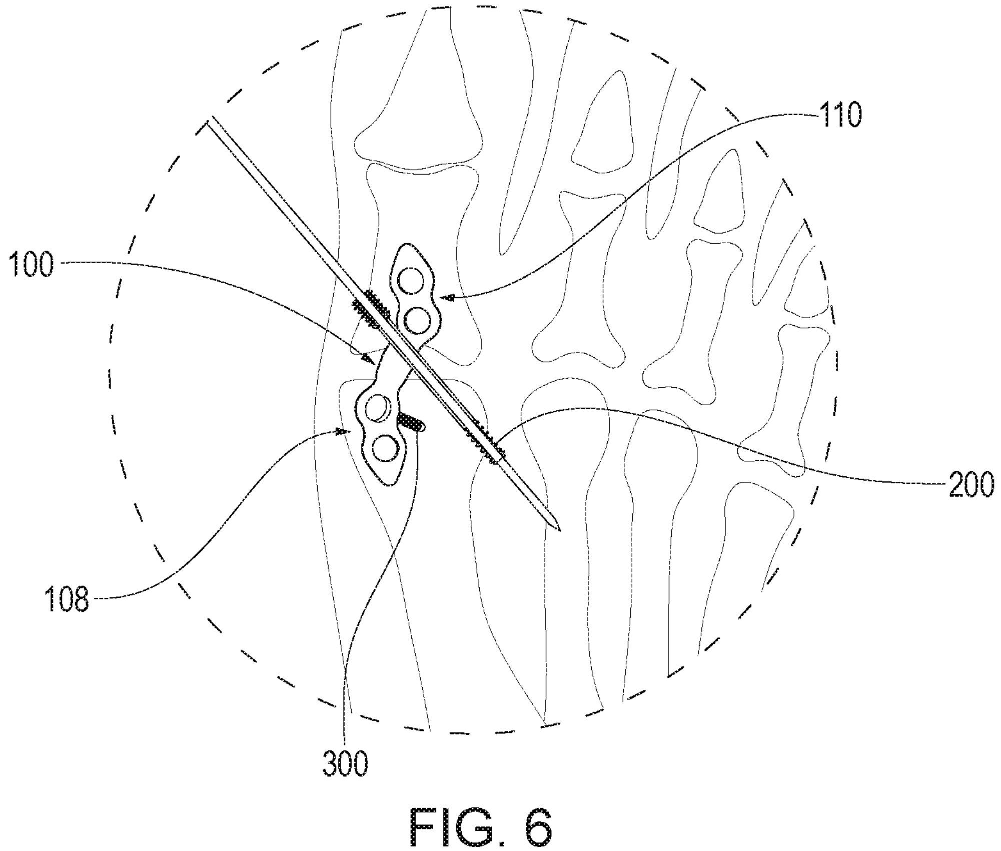
FIG. 6 illustrates the bone plate shown in FIG. 2 and bone anchors securing the bone plate in place in the bone of a foot.
Figure 7A:
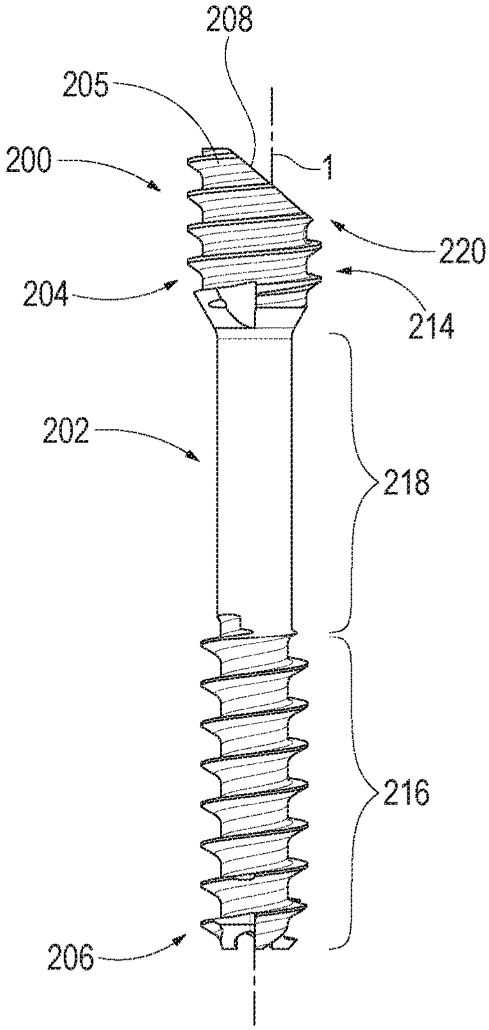
FIGS. 7A and 7B are side and top perspective views, respectively, of a crossing anchor of a bone fixation system according to an embodiment of the present disclosure.
Figure 7B:
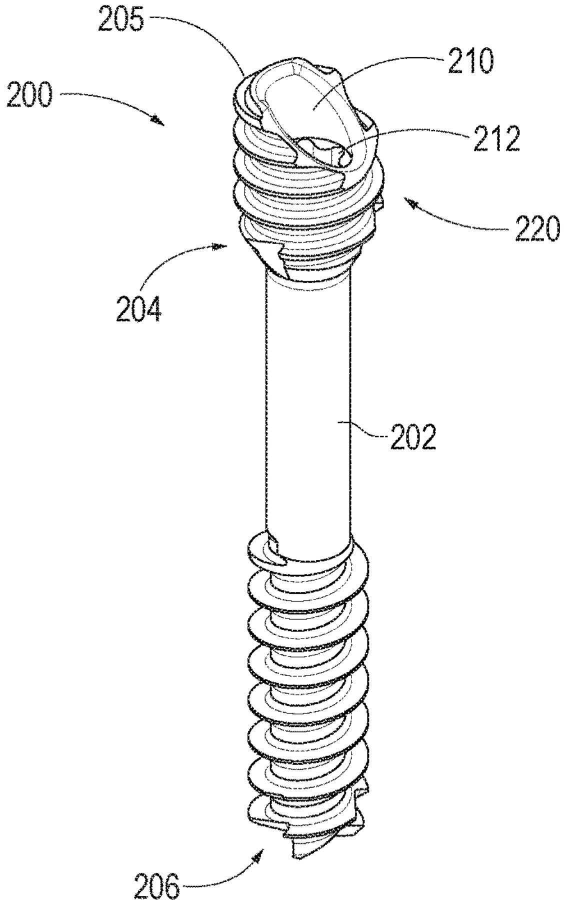

FIGS. 7A and 7B illustrate a crossing anchor 200 according to an embodiment of the disclosure. The crossing anchor 200 is configured to be inserted into a first bone segment and engage a second bone segment that is adjacent the second bone segment. The crossing anchor 200 may span a joint between adjacent foot bone segments. The crossing anchor 200 is configured to be inserted in the anatomy inferior to the bone plate 100 when the bone plate 100 is fixed in place with bone anchors 300, 350. The crossing anchor 200 has head 205 and a shaft 202 that extends from the head 205. The crossing anchor further has a proximal end 204 and a distal end 206 spaced from the proximal end 204 along the central axis 1. The proximal end 204 includes the head 205 with a proximal beveled surface 208 that is angled with respect to the central axis 1. Also included is a cavity 210 that extends into the head 205 along the central axis 1 toward an engagement feature 212 configured to engage a distal end of a driver. The engagement feature may be any feature configured to engage a driver, such as lobed, hex, star, plus, etc. In the embodiment shown, the crossing anchor 200 is only partially threaded at a proximal region 214 and a distal region 216 with a central portion 218 of the shaft 202 being unthreaded. The central portion 218 of the shaft 202 is configured to span the space between opposing faces of the proximal and distal bones, as shown in FIG. 6.

Figure 8A:
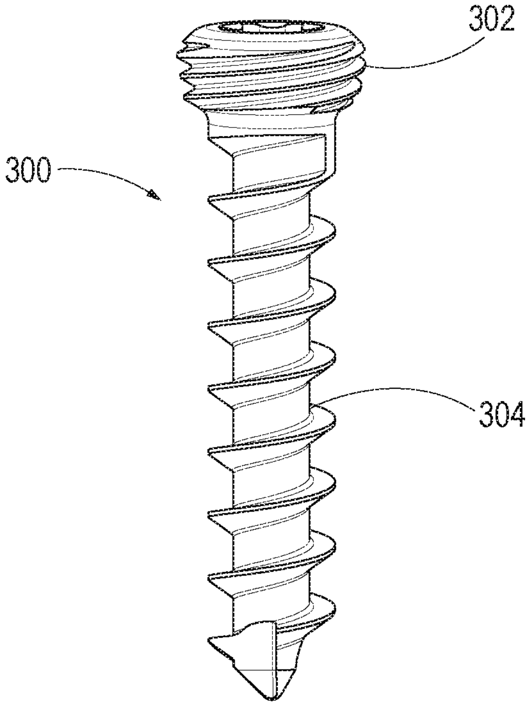
FIG. 8A illustrates a bone anchor according to an embodiment of the present disclosure.
Figure 8B:
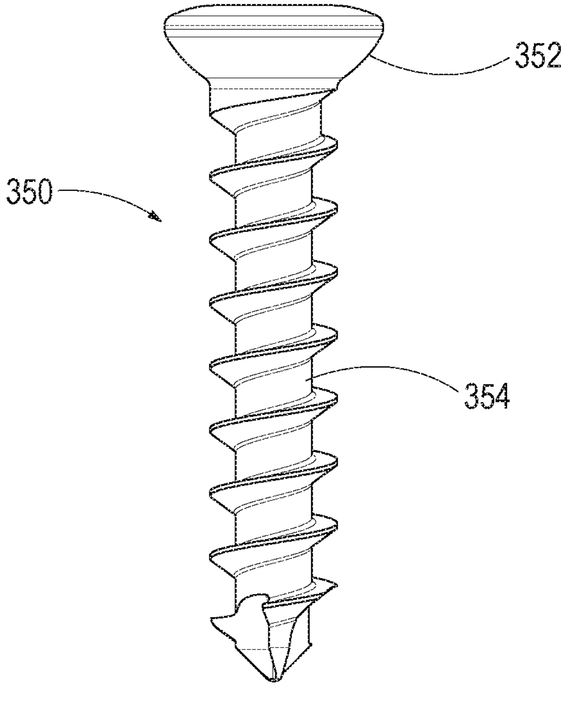
FIG. 8B illustrates a bone anchor according to another embodiment of the present disclosure.

FIGS. 8A and 8B illustrate bone anchors used to fix the plate 100 to the bones as shown in FIG. 6. More specifically, FIG. 8A shows a bone anchor 300 having a head 302 and a threaded shaft 304 that extends from the head 302. The head 302 of anchor 300 is threaded to lock into a hole of the bone plate 100. For instance, the threads on the head 302 of the bone anchor 300 are configured to engage the threads on an inner surface of the through-holes in the bone plate 100.

FIG. 8B shows a bone anchor 350 having a head 352 and a threaded shaft 354 that extends from the head 352. Here, the head 352 is not threaded to compress the bone plate 100 toward the bone when the bone anchor fully engages the through-holes of the bone plate 100. The system may include two bone anchors 300, 350 for the proximal fixation portion 108 and two bone anchors 300, 350 for the distal fixation portion 110 of the bone plate 100.

Figure 9:
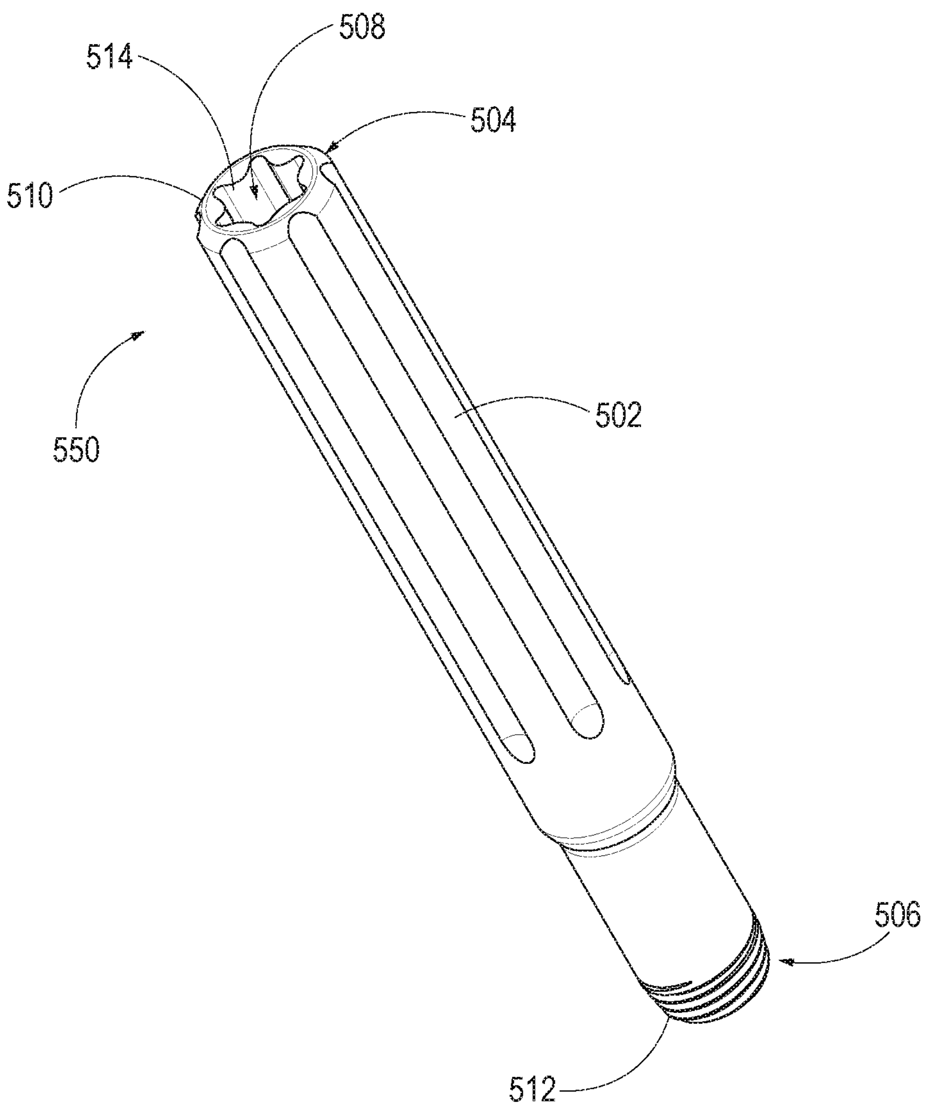
FIG. 9 illustrates a drill guide according to an embodiment of the present disclosure.
Figure 13:
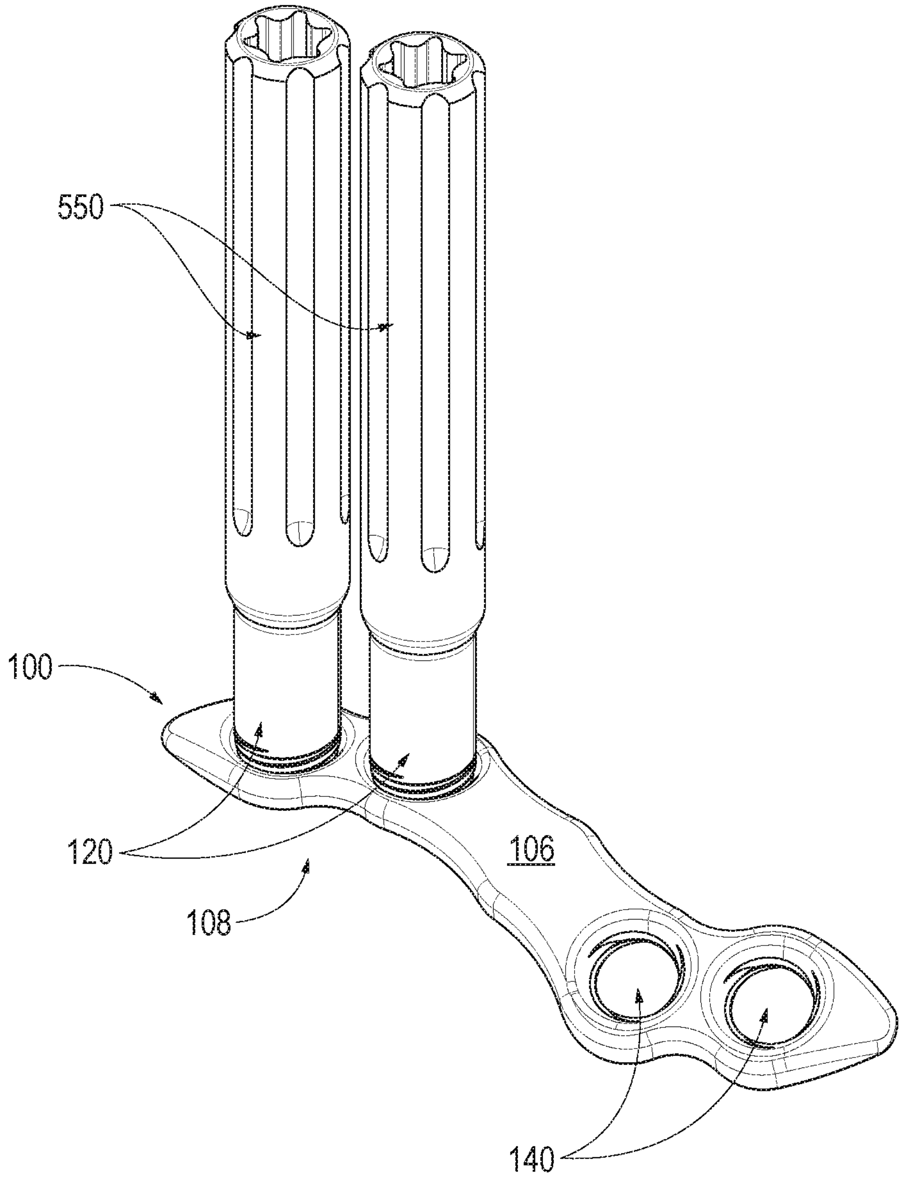
FIGS. 13-26 illustrates a method of using the targeting instrument and arm shown in FIGS. 10-12 to implant a bone fixation system according to an embodiment of the present disclosure.

FIG. 9 illustrates a drill guide 550 configured to engage the through-holes 120, 140 of the bone plate 100, as shown in FIG. 13. The drill guide 550 may be an elongated body 502 that has a proximal end 504, a distal end 506 spaced apart from the proximal end 504, and a cannulation 508 that extends from the proximal end 504 to the distal end 506. The cannulation 508 in configured to receive a drilling instrument and anchor therethrough. The proximal end 504 may include an engagement feature 514 to receive a driver. Further, a proximal-most end of the drill guide 550 includes an engagement surface 510 that can abut a shoulder in the targeting instrument 400 as described below. The distal end 506 includes a tip 512 configured to threadably engage the threads on of the through-holes 120, 140 in a bone plate 100. The drill guides 550 are therefore configured to threadably engage the bone plate 100. In the bone fixation system described herein, there is typically two drill guides 550 for each side of the bone plate 100 that has through-holes. More specifically, the system includes first and second distal drill guides 550 configured to engage through-holes in the distal fixation portion 110 of the bone plate 100 and first and second drill proximal guides 550 configured to engage through-holes in the proximal fixation portion 108 of the bone plate 100. In alternative configurations, the cannulation is such that it permits a bone anchor to pass through the drill guides 550 so that anchors 300, 350 can engage the bone plate 100 while the guide is coupled to the bone plate.

Figure 10:
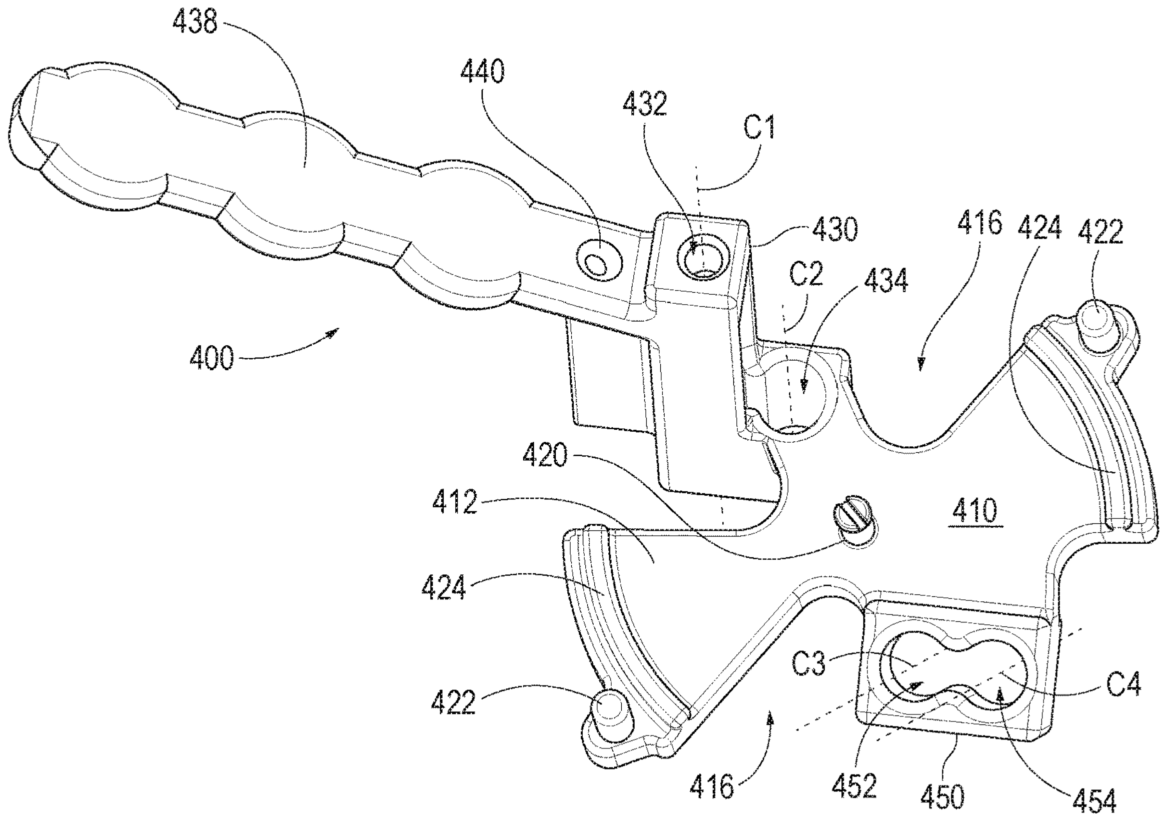
FIGS. 10-11 illustrate a targeting instrument according to an embodiment of the present disclosure.
Figure 11:
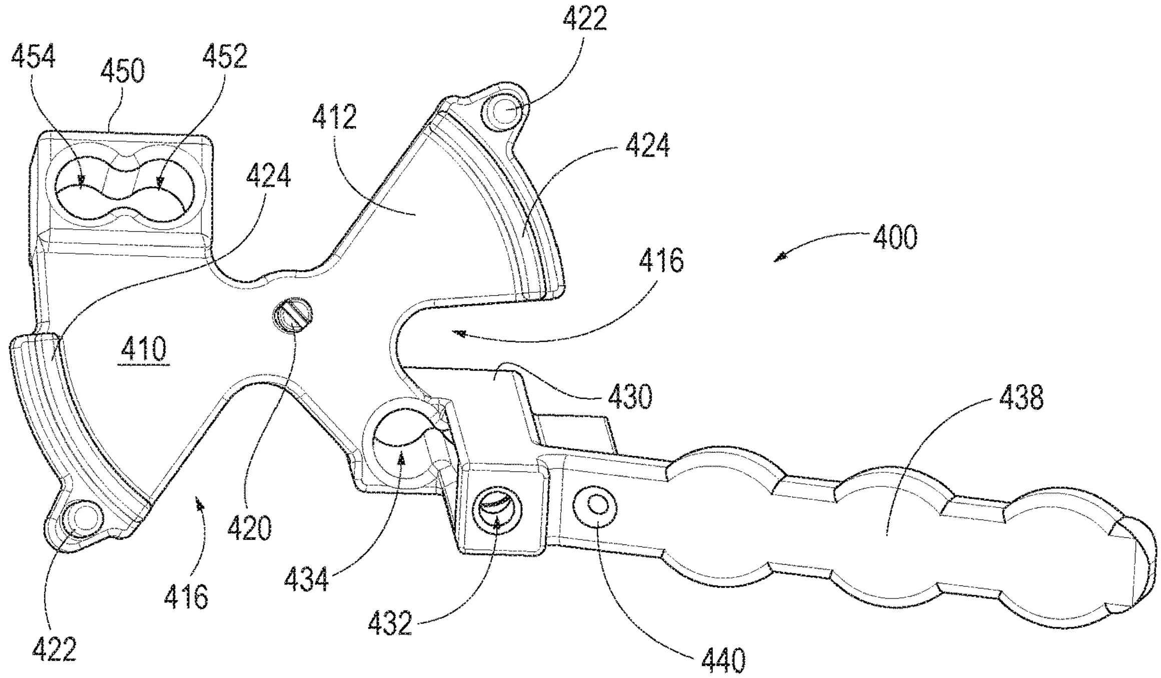

Referring to FIGS. 10 and 11, the bone fixation system 10 includes a targeting instrument 400 having a platform 410, a proximal guide body 430 coupled the platform 410, and a distal guide body 450 coupled to the platform 410 and generally opposite the proximal guide body 430. In an alternative configuration, however, the targeting instrument 400 could include a one guide body, such as guide body 430, thus omitting the distal guide body 450. Thus, the targeting instrument could include the platform 410 and one or more distal guide bodies coupled to the platform.

The platform 410 includes a platform body with a generally flat upper surface 412, a central portion 414, and one or more wings 416 that extends from the central portion 414 outwardly. Thus, the platform 410 may have a single wing or two wings (e.g. a left wing and a right wing) as shown. The wings 416 are shown as having a wedge shape. However, other shapes may be used as need and wedge shape shown is not limiting. The platform 410 has one or more engagement elements (or "first engagement elements") configured to engage with one or more engagement elements (or "second engagement elements") on the anchor targeter 500. As shown, the first engagement elements may include a pivot post 420, a guide post 422, and curved ridge 424. The pivot post 420 extends from the upper surface 412 of the platform 410 at the central portion 414. As illustrates, each wing 416 includes a guide post 422 extending from the platform 410 and spaced toward or along an outer edge of the platform 410, and a curved ridge 424 extending from the platform 410 in the same direction that the pivot post 420 and the guide post 422 extend. The curved ridge 424 arcs relative to the pivot post 420. The pivot post 420, guide post 422 and curved ridge 424 engage the anchor targeter 500 as further described below. However, depending on the type of anchor targeter 500 used, the platform 410 may include one or more posts (without a particular curved ridge) or other types of engagement elements.

The proximal guide body 430 has one or more guide channels for receiving one or more drill guides 550, respectively. For example, the proximal guide body 430 has a first guide 432 channel (also referred to as proximal guide channel) for receiving a first drill guide 550, and a second guide channel 434 for receiving a second drill guide 550. The proximal guide channels 432, 434 extend along a respective proximal guide axes C1, C2 that are coincident with the axes of the through-holes of the bone plate 100 (when coupled together as shown in FIG. 13). Each guide channel 432, 434 is sized and shaped to permit a bone anchor 300 is pass completely through the respective guide body 430. The proximal guide body 430 also includes a shoulder 436 (FIG. 14B) configured to contact a surface 510 of the proximal-most end of a drill guide 550 to set a distance of the target instrument 400 relative to the bone plate 100. In addition, the targeting instrument 400 also includes a gripping arm 438 extending from the proximal guide body 430.

The proximal guide body 430 also includes a stabilization guide channel 440 configured to receive a wire. The stabilization guide channel 440 has a trajectory along an axis D1 that does not intersect the bone plate 100 when the targeting instrument 400 is coupled to the bone plate 100. In the example shown, the guide channels 432, 434 and the stabilization guide channel 440 may be aligned along a common plane (not shown) that extends perpendicular to the superior surface of the platform 410.

The distal guide body 450, when present, also has one or more guide channels for receiving one or more drill guides. For example, the distal guide body 450 has a first guide channel 452 for receiving a first drill guide 550, and a second guide channel 454 for receiving a second drill guide 550. The one or more distal guide channels 452, 454 extending along a respective distal guide axes C3, C4 that are coincident with the axes of the through-holes of the bone plate 100 (when coupled together as shown in FIG. 13). Each guide channel 452, 454 is sized and shaped to permit a bone anchor 300 is pass completely through the respective guide body.

Figure 12:
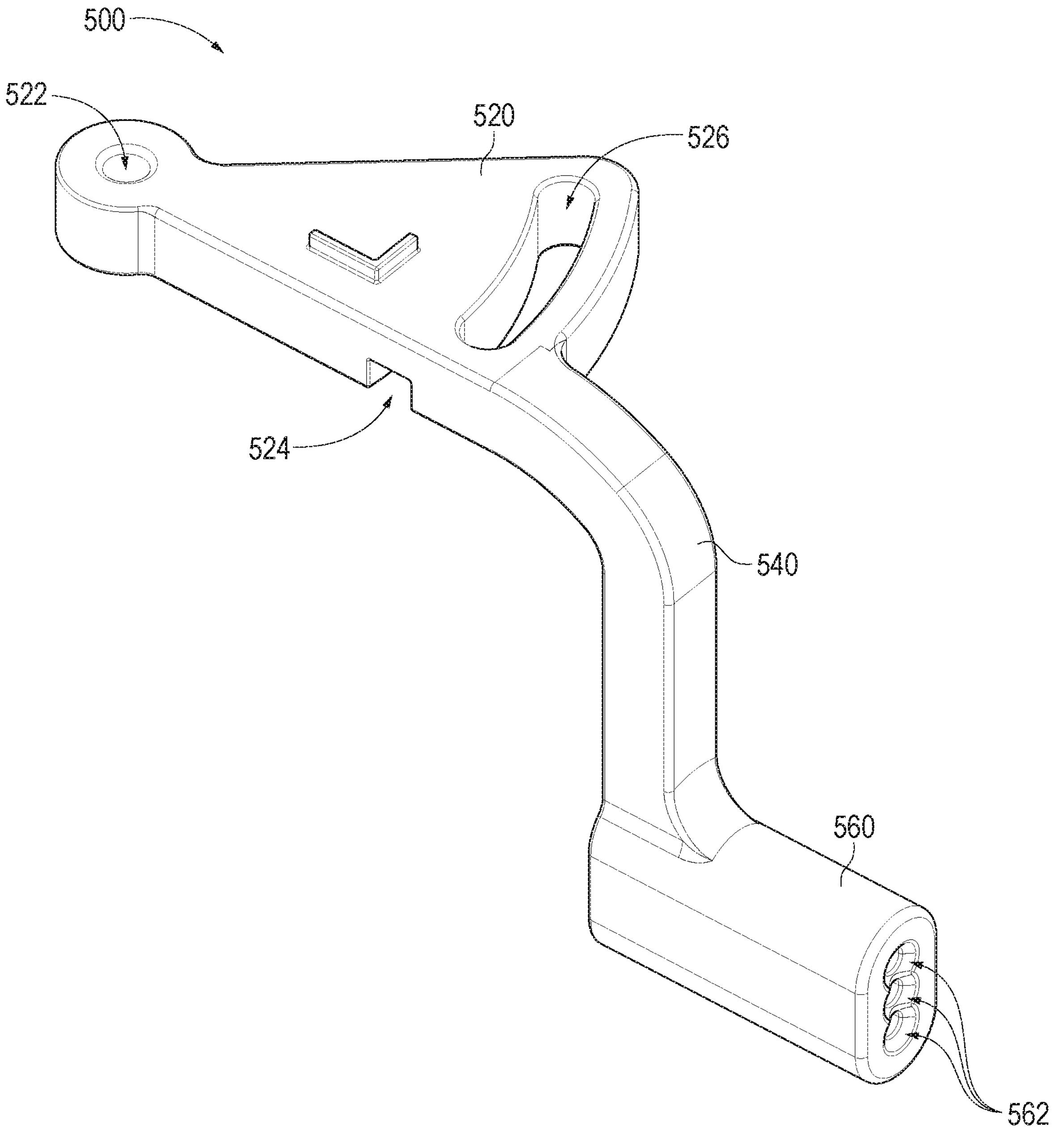
FIG. 12 illustrates a targeting arm configured to be movably coupled to the targeting instrument shown in FIGS. 10 and 11.

Referring to FIG. 12, the anchor targeter 500 is configured to guide the crossing anchor 200 into position across the joint relative to the bone plate 100. The anchor targeter 500 has a base 520 sized and shaped to fit atop the platform 410, an arm 540 extending and curving from the base 520, and an aiming body 560 at a terminal end of the arm 540. The base 520 may include one or more engagement elements configured to engage with one or more engagement elements on the targeting instrument 400. For example, as shown, the base 520 includes a bore 522 configured to couple to the pivot post 420, a first slot 524 that receives the curved ridge 424, and a second slot 526 that receives the guide post 422. Configured this way, the aiming arm 540 can rotate about the pivot post 420 to adjust the trajectory of the aiming body 560 relative to the targeting instrument 400. In other configurations, the engagement elements of the anchor targeter 500 may include one or more bores configured to receive one or more posts of the targeting instrument. Other types of engagement elements may be used to aid in securing the targeter 500 to the targeting instrument to guide the crossing anchor into position. The aiming body 560 may include one or more or a set of fixation-guide channels 562 to insert a fixation wire along with the crossing anchor can be positioned. The different channels may have different trajectory so the user can select the appropriate trajectory based on surgical procedure and specific anatomy of the patient.

In another embodiment, the anchor targeter 500 is configured to attach directly to the drill guides 550, omitting the need for the targeting instrument 400. More specifically, the system may include one or more drill guides 550 having a tip 552 configured to threadably engage holes in a bone plate 100 and a cannulation 554 that extends from the tip 552 through the drill guide 550. In such an embodiment (not shown), the alternative anchor targeter 500 includes a base configured to attach directly to one more drill guides, an aiming arm extending and curving from the base, an aiming body at a terminal end of the arm, and an aiming channel that extends through entirely through the aiming body. The aiming channel extends along a targeting axis that is inferior to and does not intersect the platform. The anchor targeter is configured to align targeting axis with a desired anchor trajectory when coupled directly to the drill guides (which are attachable to the bone plate as described above).

The surgical method is illustrated in FIGS. 13-26 and may be described as minimally invasive method for metatarsal phalangeal (MTP) joint fusion design to join the bones of the big toe together. The surgeon, or other user, prepares the target location in the joint of a foot. In this embodiment shown, the surgical procedure is intended to implant the bone plate beneath the EHL tendon so that one part of the plate is located on one side of the EHL tendon, and the other part of the plate is located on the other side of the EHL tendon. In most cases, the bone plate is intended to span the joint of the foot bone but may not be the case in all instances. The surgeon begins with forming an incision. After forming an incision, the user may may also include using minimally invasive surgical burrs to cut the bone as needed.

Referring to FIG. 13, in the operating environment, a user can couple one or more drill guides 550 into one or more through-holes of in a proximal region 108 of a bone plate 100. For example, a first proximal drill guide 550 is threadably engaged with a first through-hole 120 in a proximal region of the bone plate 100 and a second proximal drill guide 550 is threadably engaged with a second through-hole 120 in the proximal region of the bone plate 100. In some instances, the user can use the drill guide-bone plate assembly to insert the bone plate into position across the desired bone target location through the first incision. More specifically, the user can hold the drill guides and an insert a first end, which may be tapered, of the bone plate through the incision until the one or more through-holes of the proximal region of the bone plate are in position. In other instances, the surgeon may use the targeting instrument.

Figure 14A:
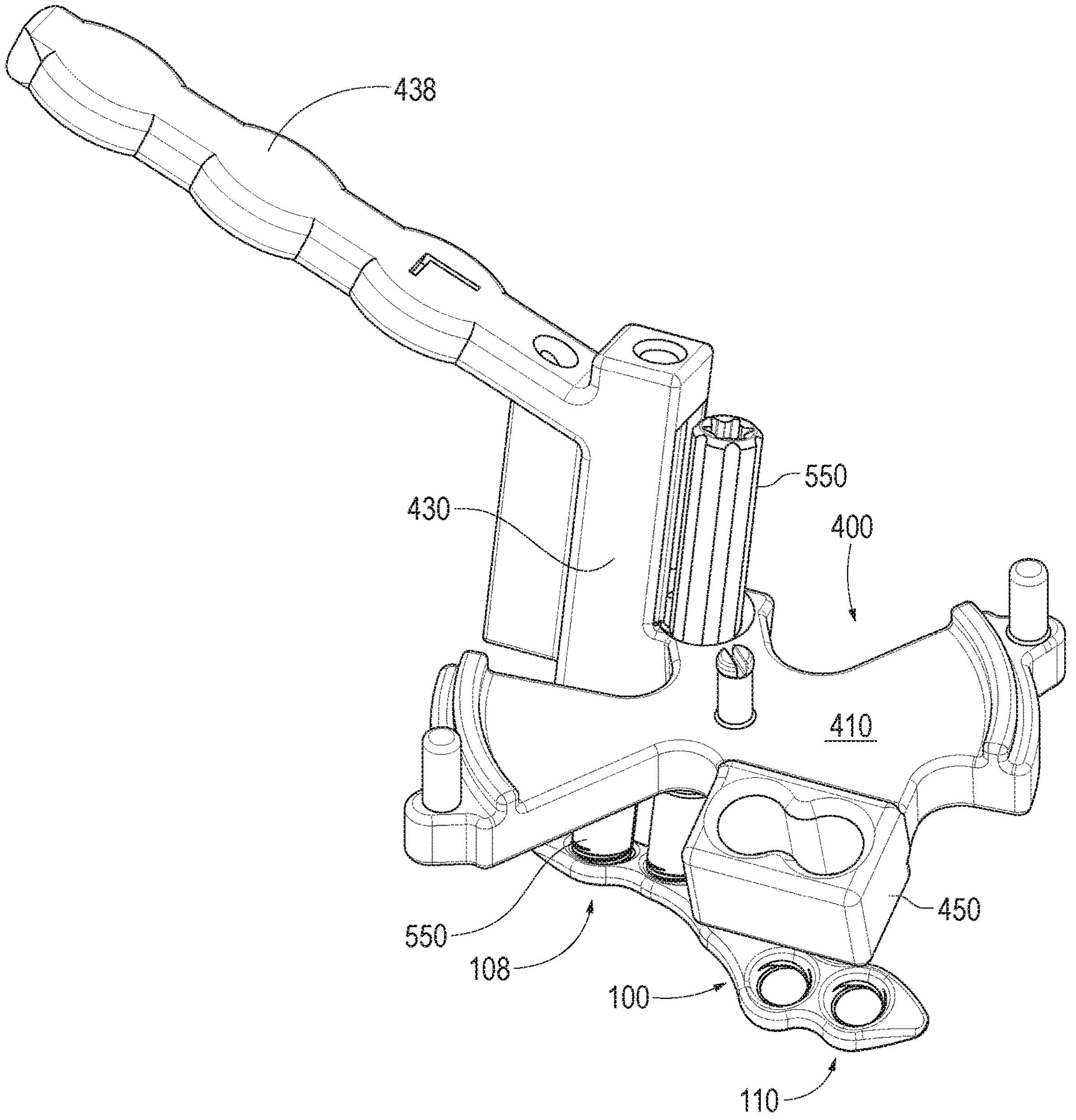
Figure 14B:
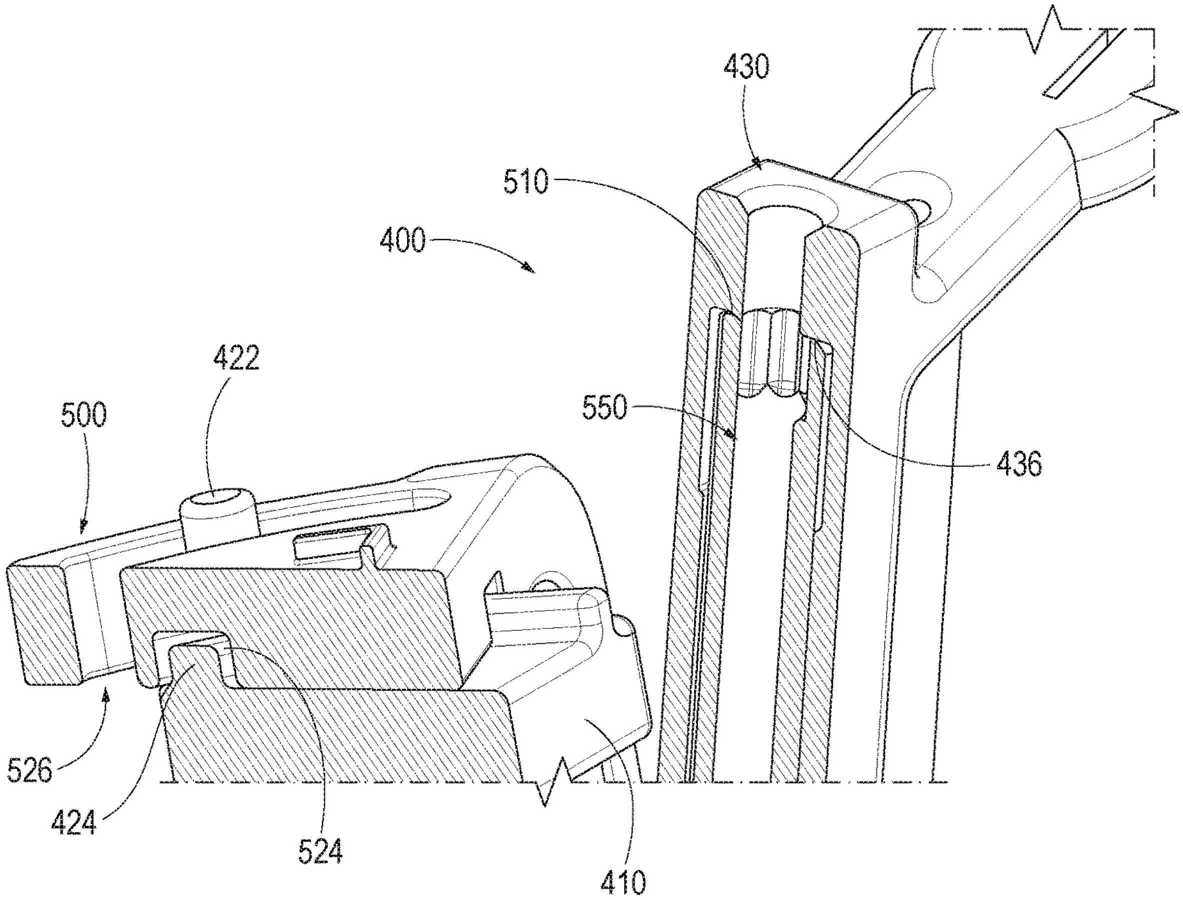
Figure 15:
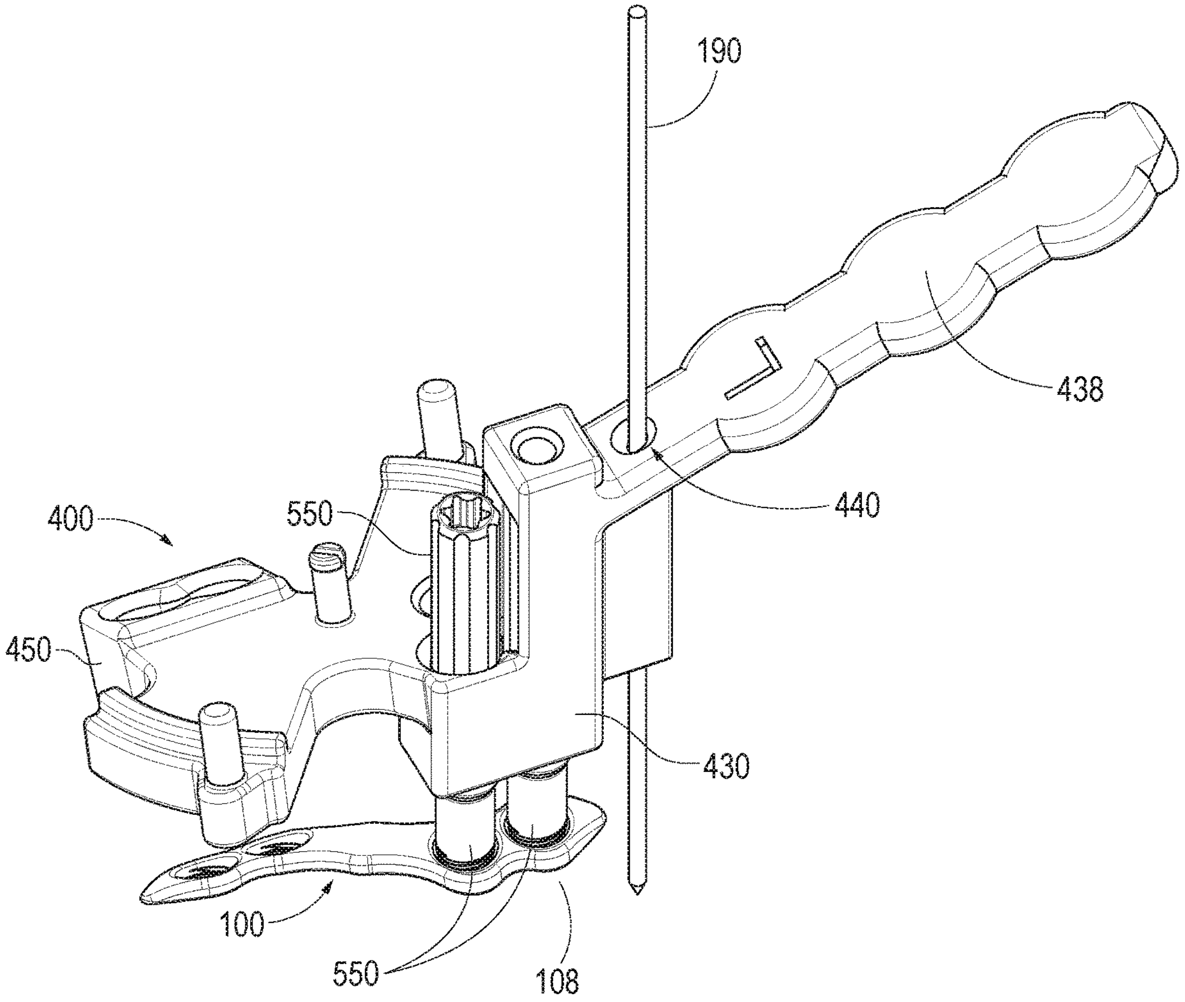
Figure 16:
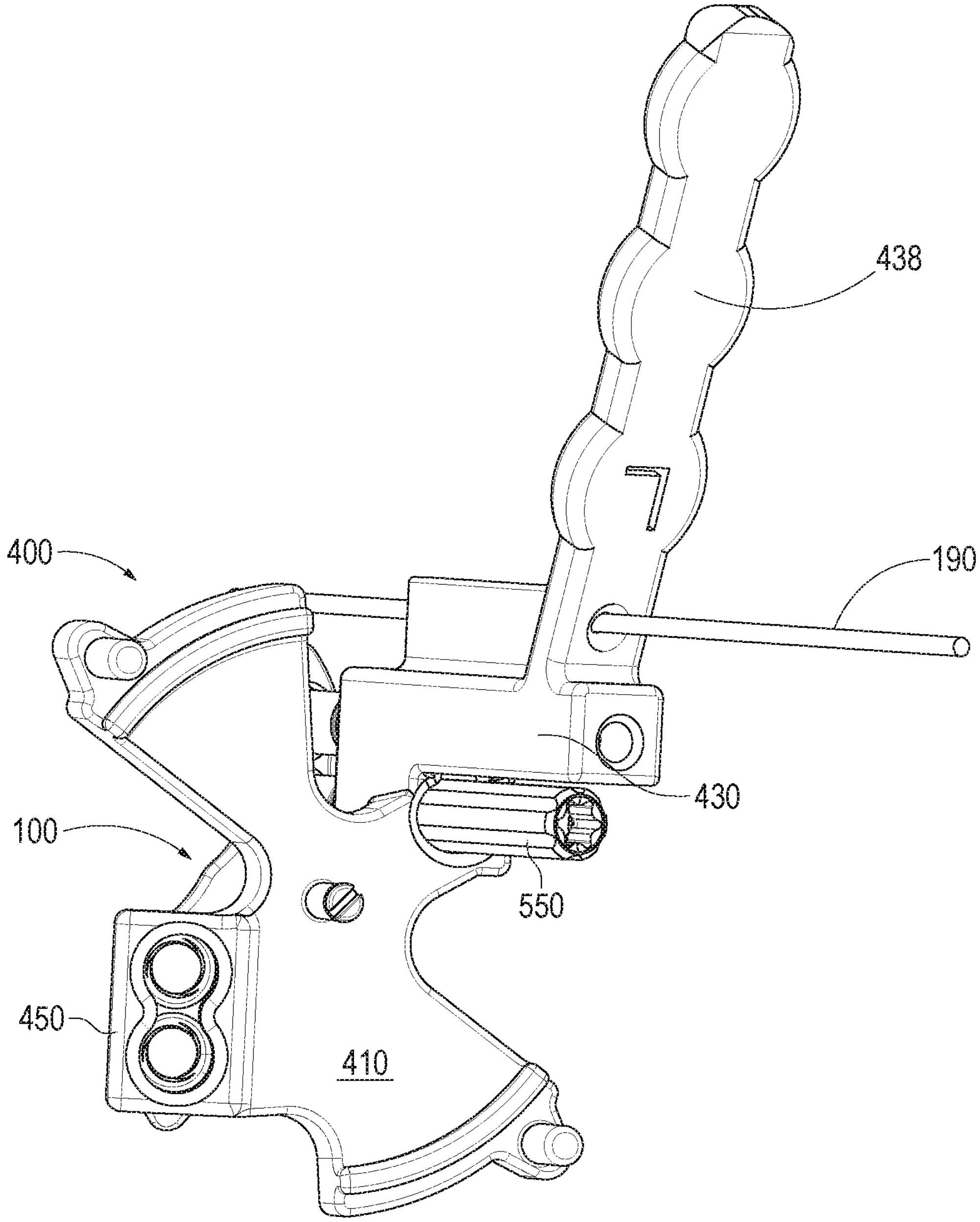

Turning to FIGS. 14A and 14B, the user can couple the targeting instrument 400 by inserting the proximal drill guides 550 into the proximal channels 432, 434 of the proximal guide body 430 of the target instrument 400. In FIG. 14B, which is a detailed cross-sectional view of the assembly shown in FIG. 14A, the targeting instrument 400 slides along the drill guides 550 until the proximal surface 510 of the drill guides abuts the shoulder 436 of the proximal guide body 430 of the targeting instrument 400. This, in turn, sets the distance of the targeting instrument 400 relative to the bone plate 100. As can be seen in this set of figures, the proximal guide channels 432, 434 extend along axes C1, C2 that correspond to the axes of the through-holes of the bone plate 100. Next, the user can position the bone plate 100 into the target location of the joint with the targeting instrument 400 and drill guides 550 coupled to the bone plate 100. This involves positioning an end (which may be tapered) of the bone plate 100 through the incision on the proximal side of the joint or target location if the bone plate is not intended to span a joint. Or it could be placed on the distal side of the joint first. As shown in FIG. 15, a stabilizing wire 190 is inserted through a wire channel 440 of the targeting instrument 400, which in turns, holds the assembly of the targeting instrument 400 and bone plate 100 in place relative to the bone. Next, the user can form a separate second incision, such when the assembly is shown in FIG. 16, in the tissue at a location that is distal (or proximal as needed) with respect to the proximal region of the bone plate 100. This provides access so that the two distal anchors 300 can be placed in the intended through-holes of the bone plate 100.

Figure 17:
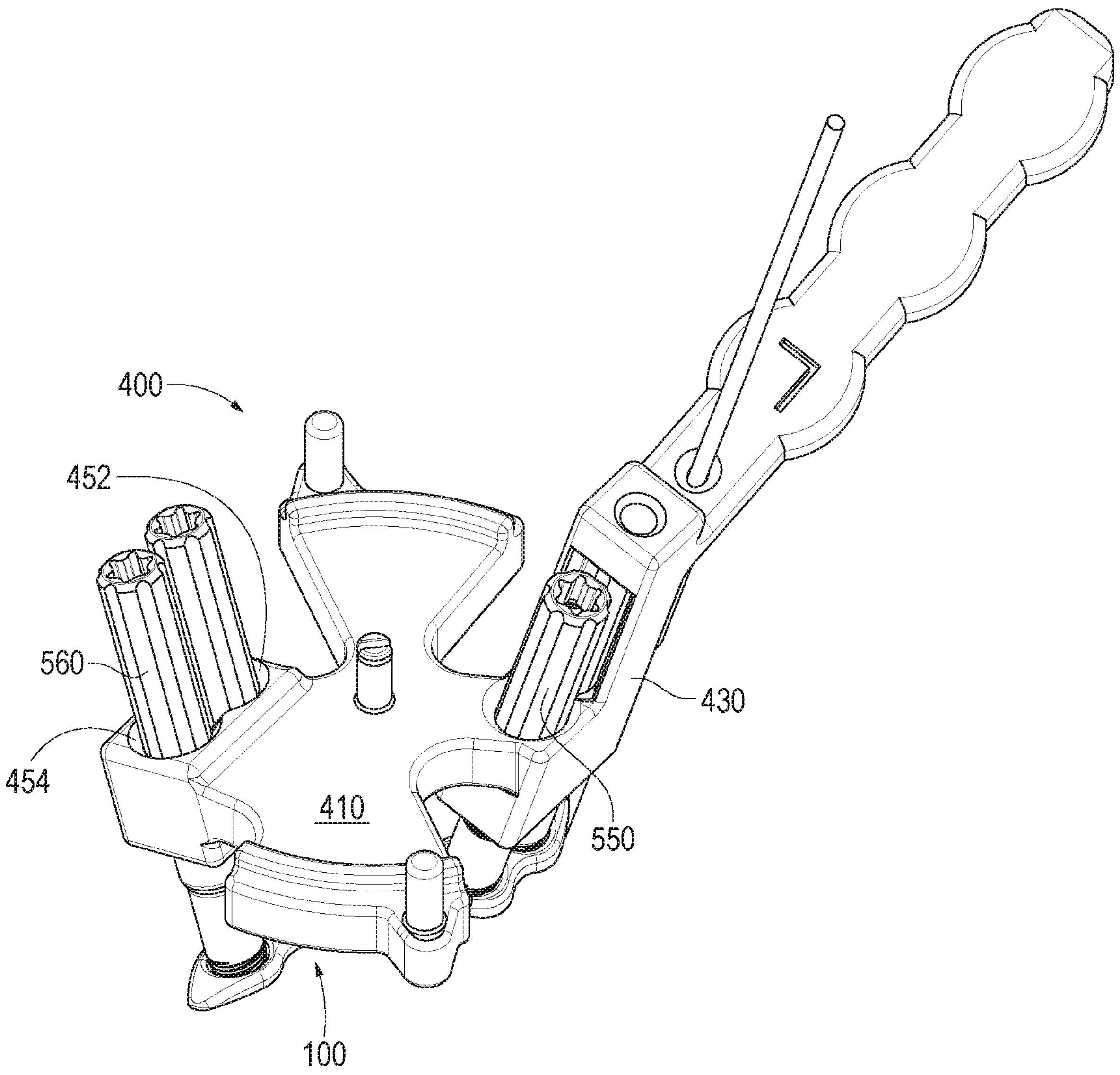

In FIG. 17, the user can insert one or more distal drill guides 550 into one or more distal channels 452, 454 of the targeting instrument 400. For example, a first distal drill guide 550 is inserted through the first distal guide channel 452 of the targeting instrument 400 and a second distal drill guide 550 is inserted through the second distal guide channel 454 of the targeting instrument 400. Using a drill, the user can then drill holes in the target location of the bone through the distal drill guides 550. Once the holes are formed in the bone, the distal drill guides 550 are removed from the guide channels 452, 454, as shown in FIG. 18.

Figure 18:
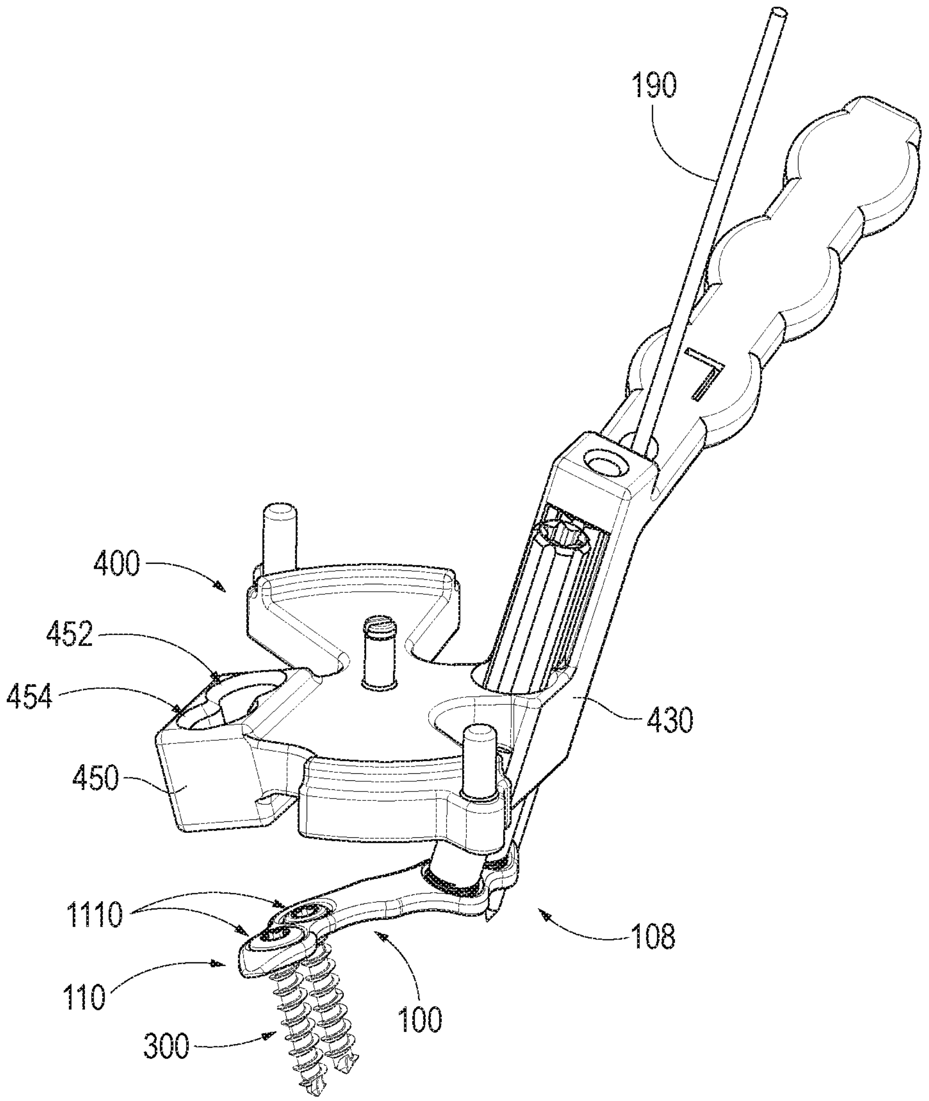

Continuing with FIG. 18, when the drill guides 55-0 are removes the user can insert one or more bone anchors 300 into the bone through the one or more through-holes in a distal region of the bone plate 100. More specifically, a first distal bone anchor 300 is inserted into a first through-hole of the bone plate 100 (in the distal portion), and a second distal bone anchor 300 is inserted in the second through-hole of the bone plate 100 (in the distal portion). Here, one bone anchor could be a locking anchor, and the other bone anchor could be a compression anchor. Alternatively, both anchors could be the same type anchors, e.g. two locking anchors or two compression anchors.

Figure 19:
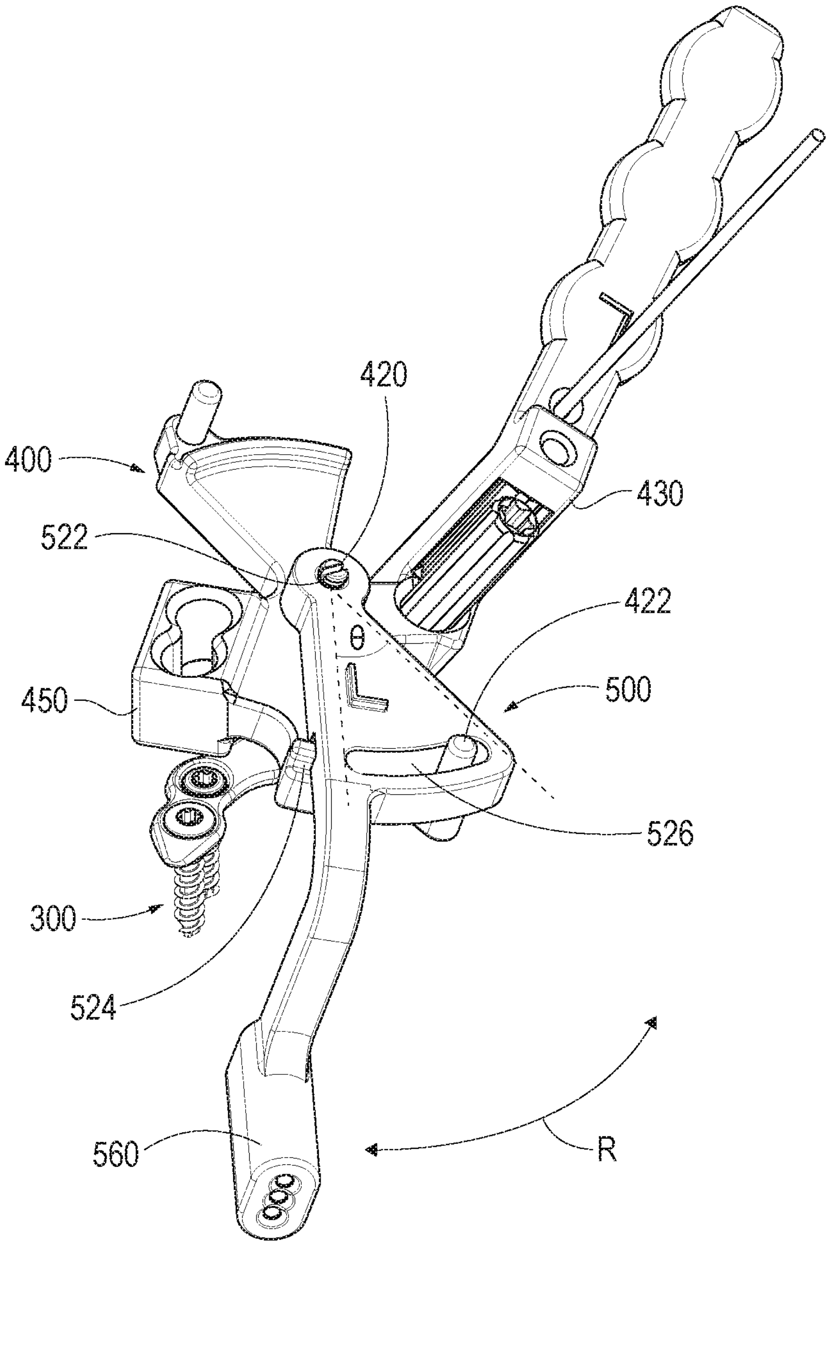
Figure 20:
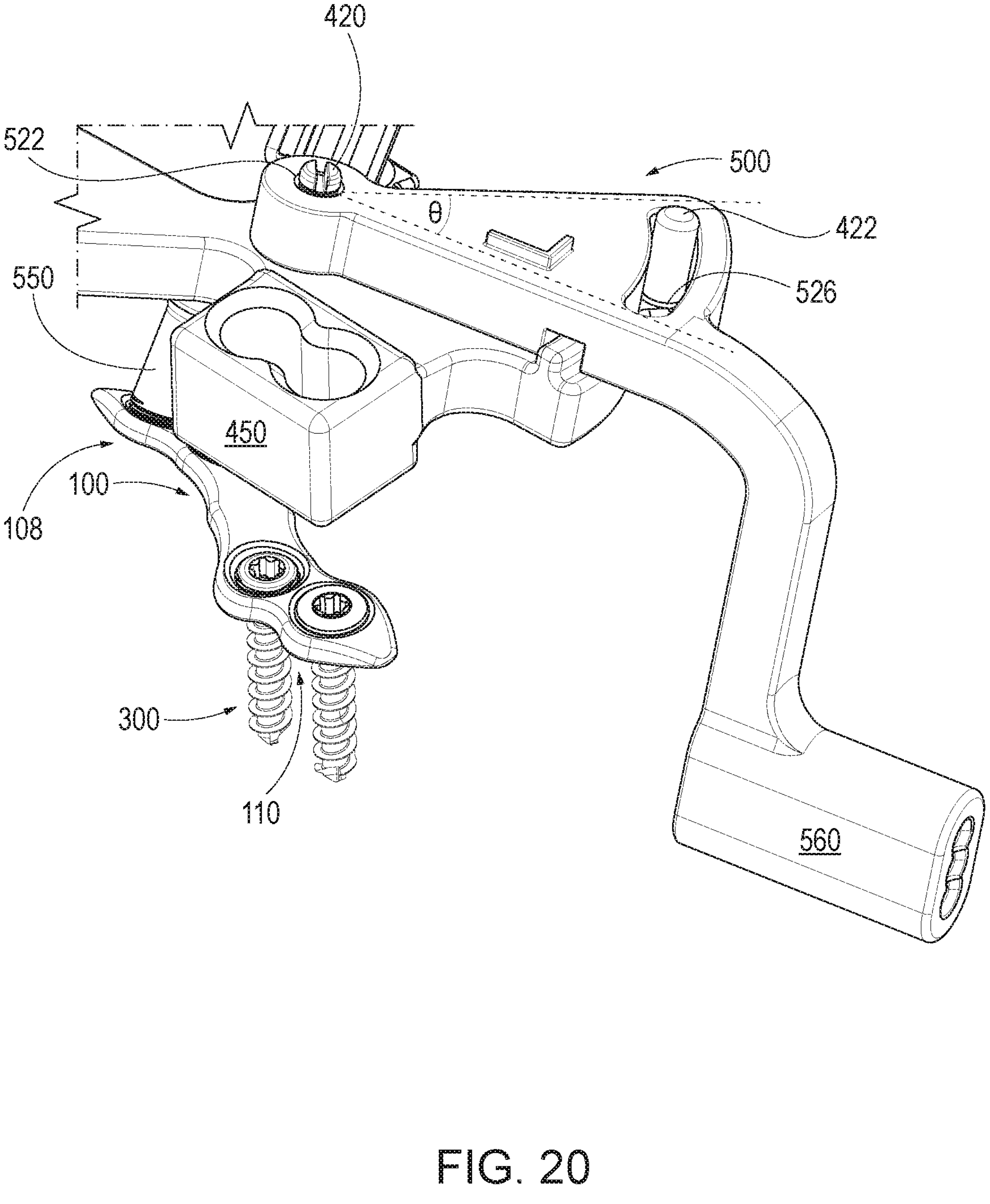

FIGS. 19 through 25 illustrate compressing the joint, generally. In the FIG. 19, the user couples the anchor targeter 500 to the target instrument 400. More specifically, the targeter 500 is placed so that the pivot post 420 engages a bore 522 in the base of the targeter 500, a first slot 524 receives the curved ridge 424, and a second slot 526 that receives the guide post 422. In the example shown, the targeter 500 has three (or more or less) different depths plantar/dorsal for the surgeon to use based on patient anatomy using the channels 562. The targeter 500 may be locked in place via a central pivot post 420 and targeting instrument 400. As shown in FIGS. 19 and 20, configured this way, the aiming arm 540 can rotate in a direction R about the pivot post 420 to adjust the trajectory of the aiming body relative to the targeting instrument 400. The arc and extent of the slot 526, 524 and ridge 424 can define an angle of rotation θ of the targeting 500 relative to the instrument 400. The angle of rotation θ can range between 10 degrees up to 90 degrees as needed. In other examples, the angle of rotation θ can be up to 30 degrees. Or angle of rotation θ can be greater than 30 degrees. In the embodiment shown, the anchor targeter 500 rotate through about 30 degrees of rotation about the pivot post 420. The user then rotates the targeter 500 so that a guide channel on the aiming arm 540 is aligned with a desired target trajectory.

Figure 21:
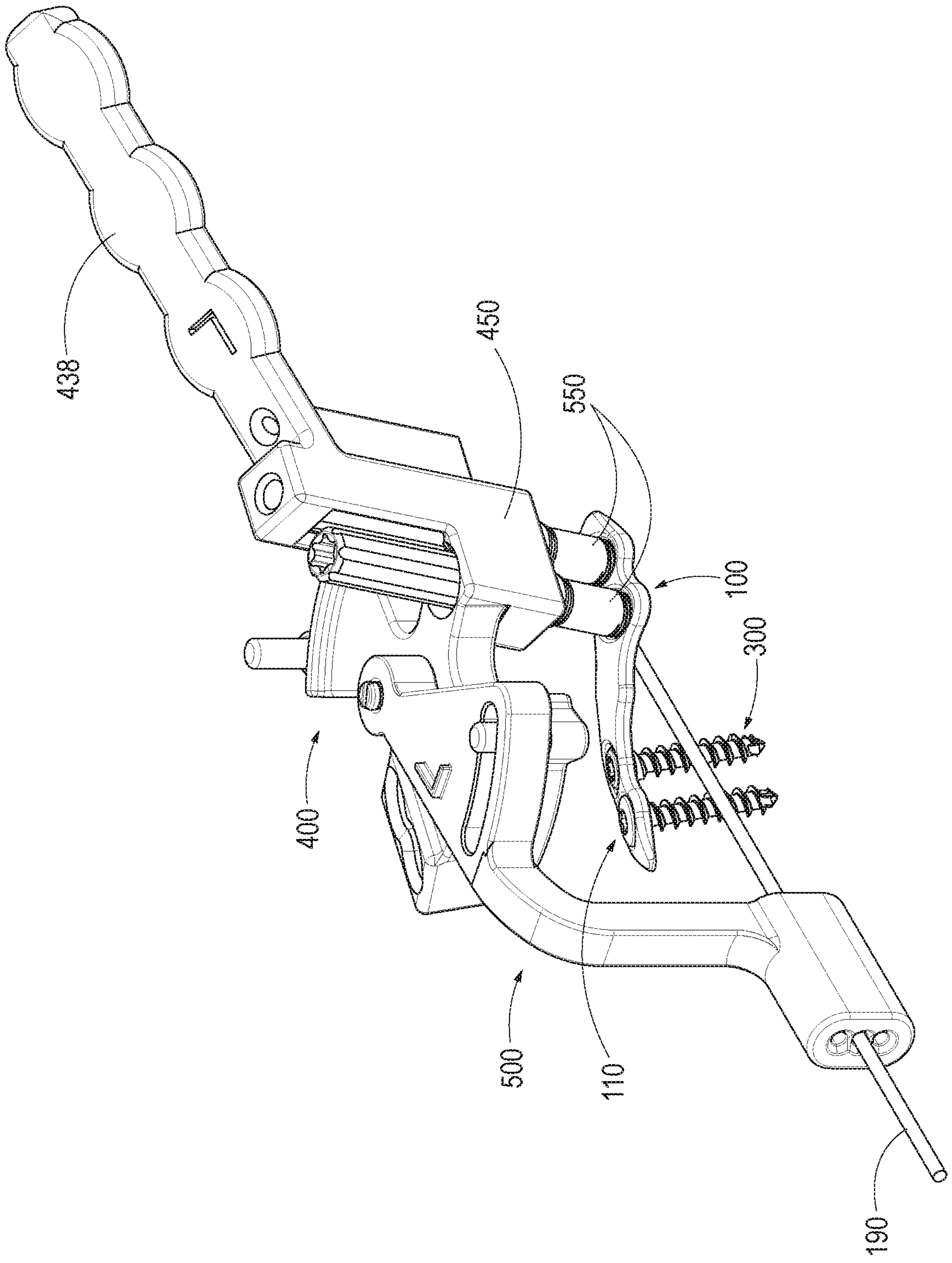
Figure 22:
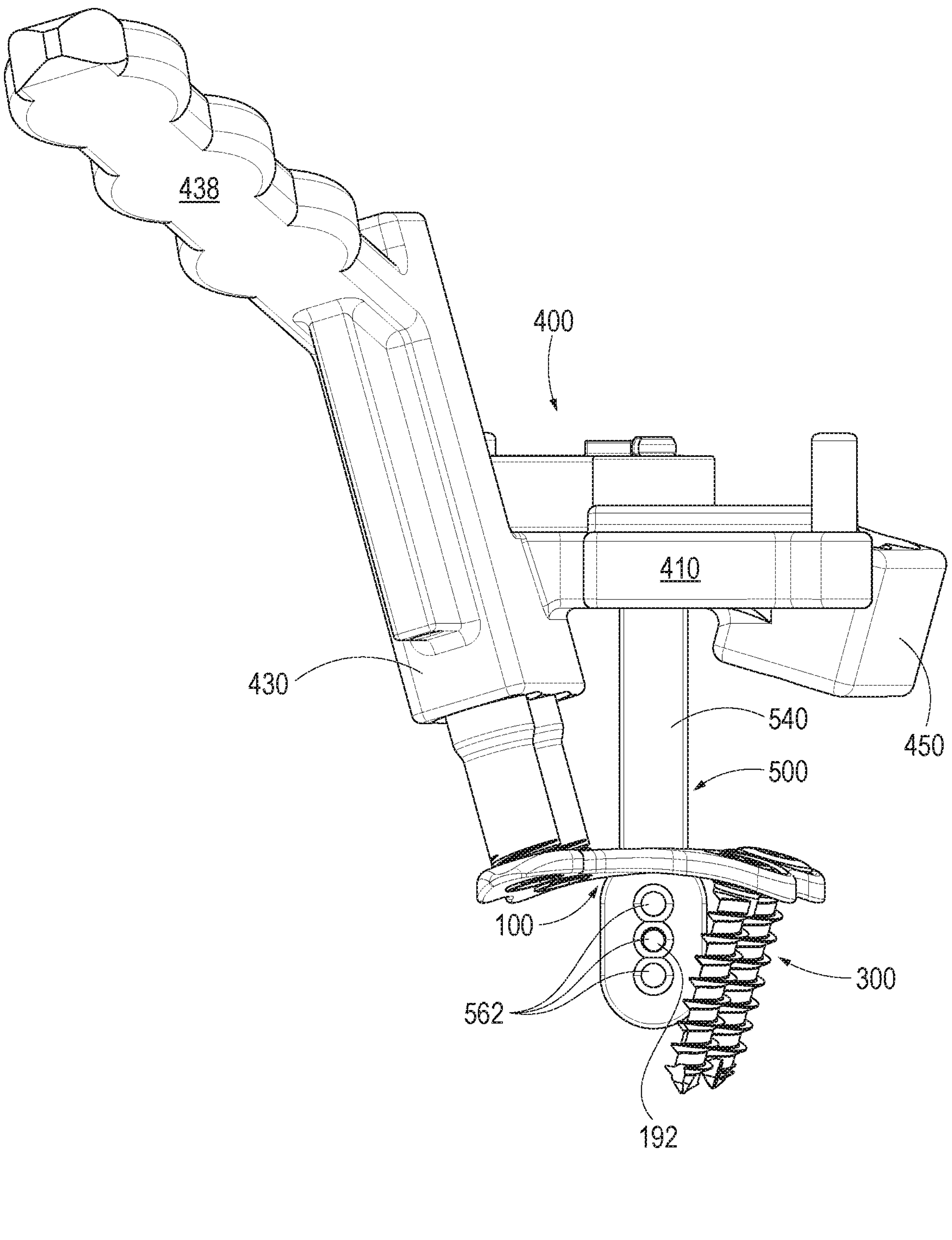
Figure 23:
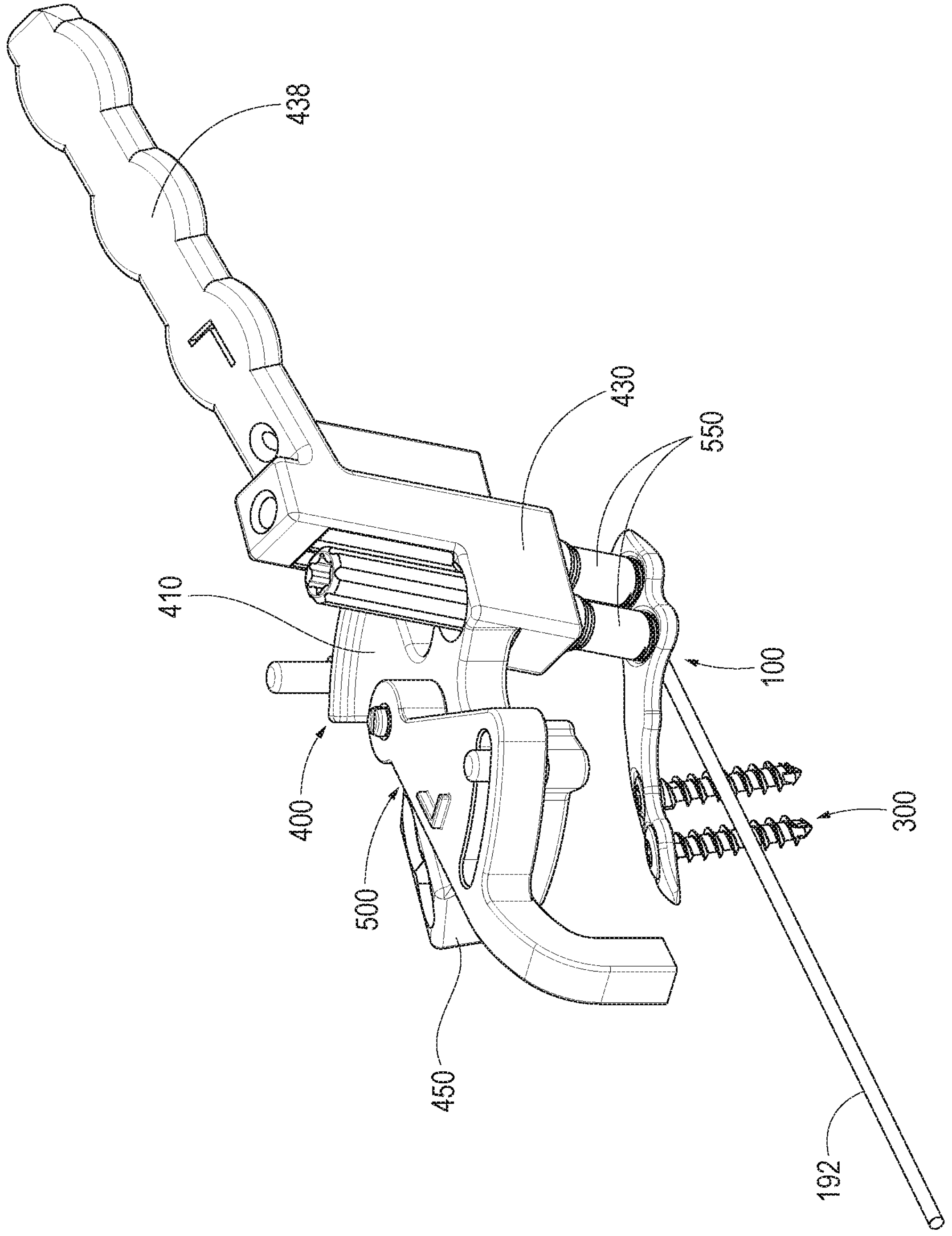

As shown in FIGS. 20-22, the user can insert a wire 192 through the aiming arm 540, via channels 562, and across the joint in a region inferior to the bone plate 100 and generally between the distal and proximal ends of the bone plate 100. The wire 192 is advanced until its distal end engages the target bone. As shown in FIG. 23, the aiming arm 540 of the targeter 500 is cut or severed and the aiming body 560 of the targeter 500 is removed from the wire 192, leaving the wire 192 in place.

Figure 24:
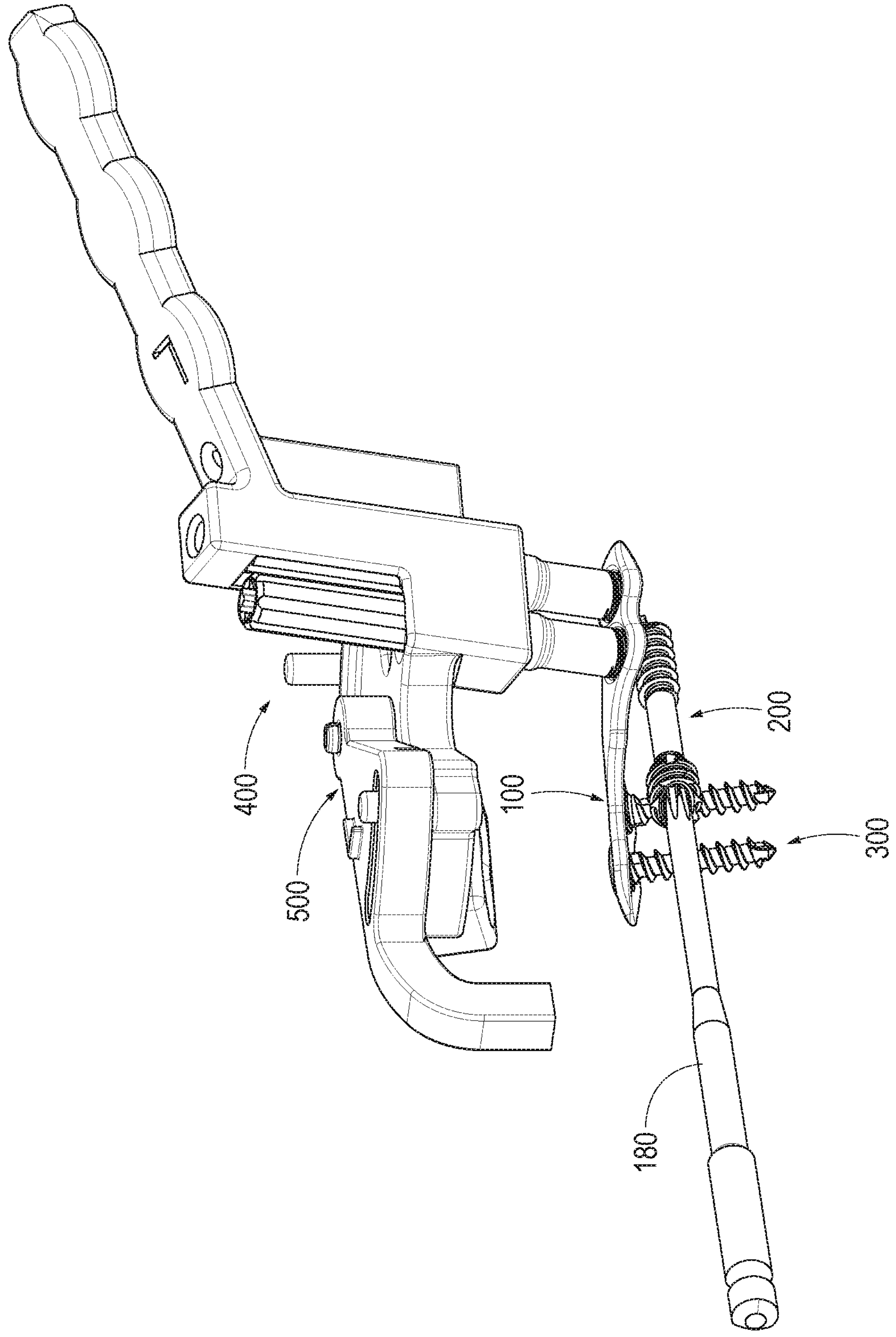
Figure 25:
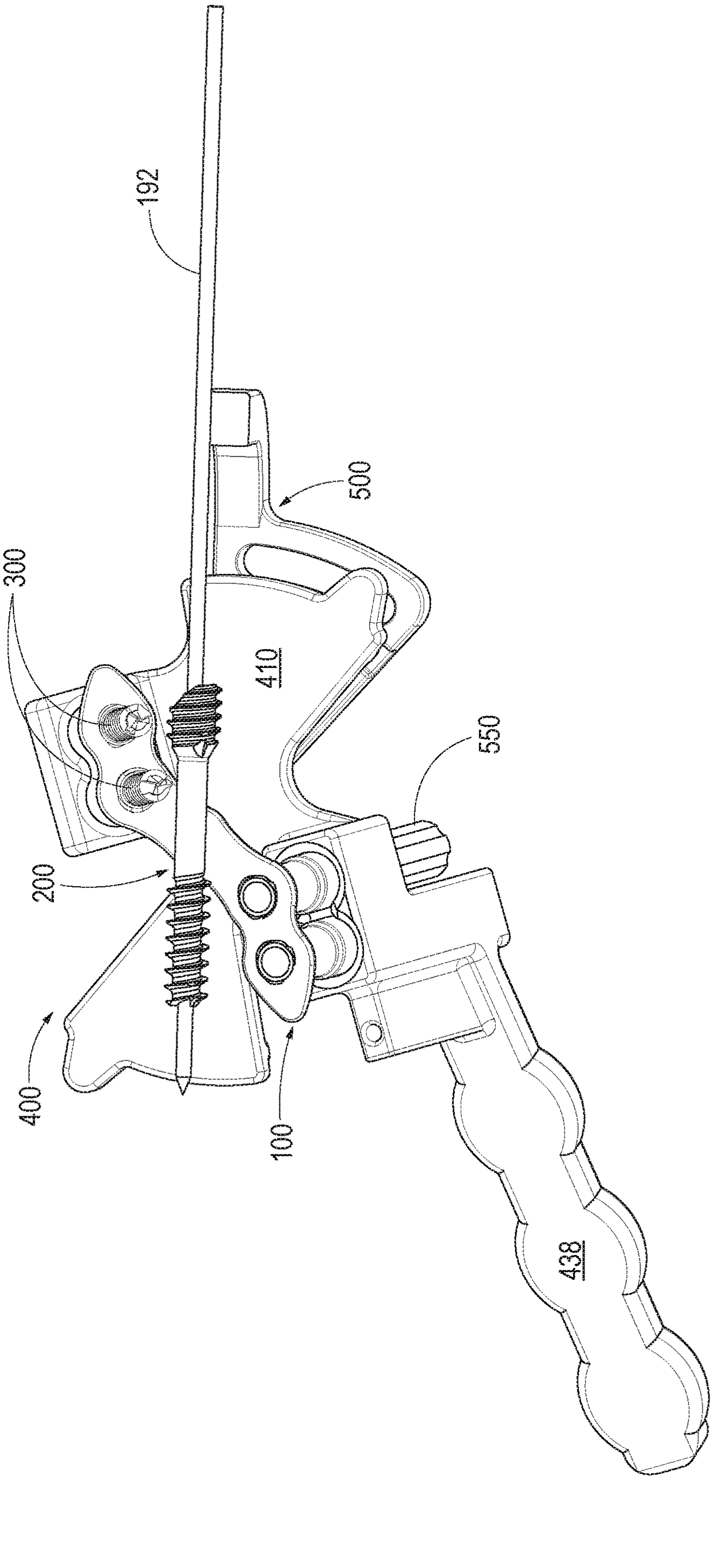
Figure 26:
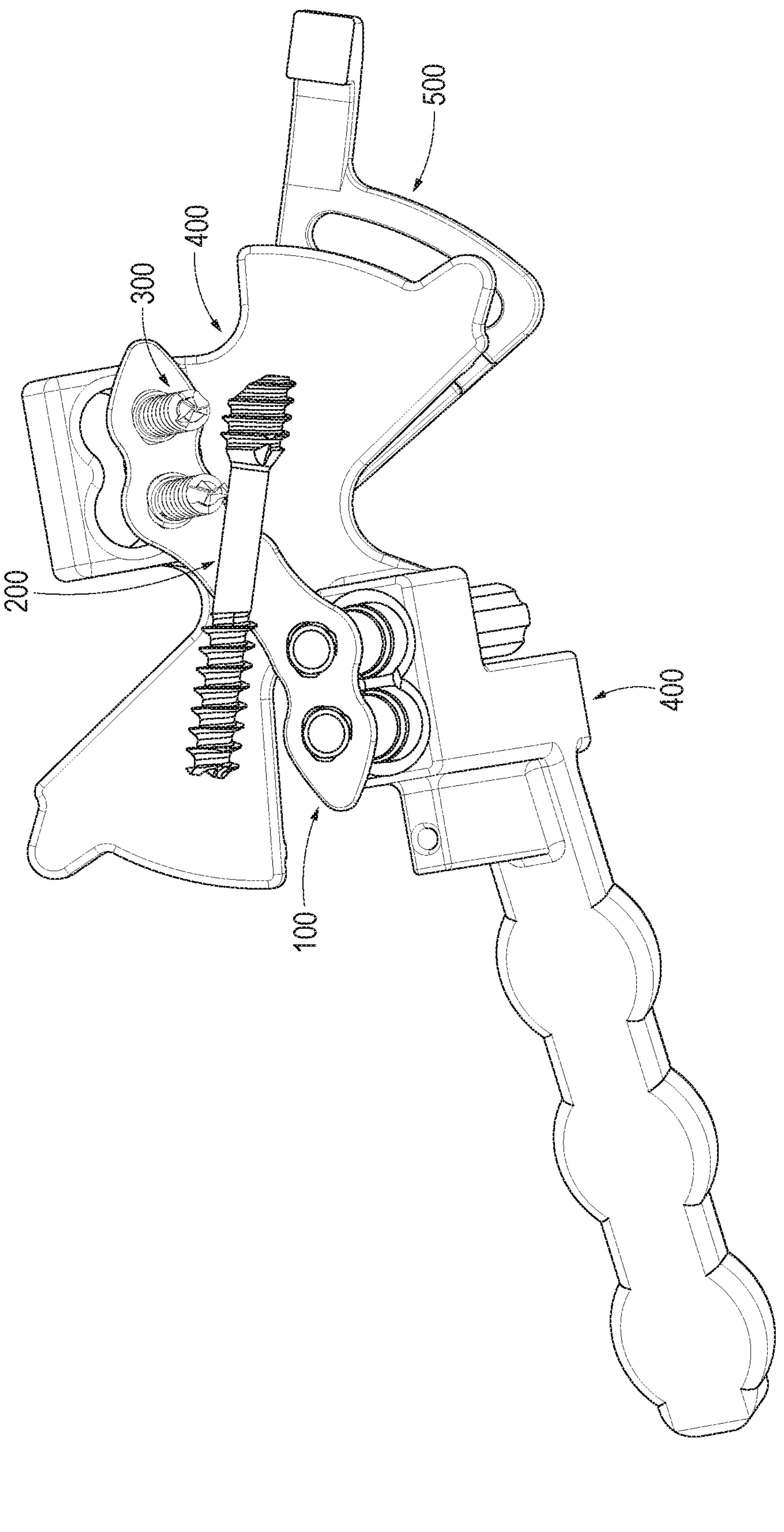

As shown in FIG. 24-26, the user can position the crossing anchor 200 over the distal end of the wire 192. This can be used with drivers 180 as needed. The driver has a mark, such as a laser-mark line, to indicate to the surgeon the location of the low side of the head bevel. This allows the surgeon to place the crossing anchor 200 such that the bevel aligns with the surface of the bone and sits flush. After the crossing anchor 200 is in position, the driver 180 is removed and the wire 192 is removed, as shown in FIG. 26. A cannulated depth gauge can be placed over the wire to measure the appropriate crossing anchor 200 length.

The user can then remove the targeting instrument 400 from the drill guides 550. The drill guides 550 can then be decoupled from the plate and anchor assembly. The user then inserts one or more bone anchors 300 through the first incision and into the one or more holes in the proximal region 108 of the bone plate 100. More specifically, the first proximal bone anchor 300 is inserted into engagement with the first through-hole in the proximal region of the bone plate 100. And the second proximal bone anchor 300 into engagement with the second through-hole of the proximal region 108 of the bone plate 100. Here, one bone anchor could be a locking anchor, and the other bone anchor could be a compression anchor. Alternatively, both anchors could be the same type.

As shown in FIGS. 27-30, when the proximal bone anchors are in place, the result is a set of anchors 300 engaged with a proximal portion of the bone plate 100, a set of anchors 300 engaged with the distal portion of the bone plate 100, and a crossing anchor 200 spanning the joint and in positioned between the shafts of all the bone anchors (without contact) and inferior to the bone plate 100 (without contacting the bone plate 100), as shown in FIGS. 27-30, the crossing anchor 200 is placed between the implanted bone anchors and inferior to the bone plate 100. In other words, the crossing anchor 200, once implanted, does not contact or touch any bone anchor or any part of the bone plate 100. Positioned this way, at least one anchor is positioned on one side of an extensor hallucis longus (EHL) tendon and at least one anchor is positioned on the other side of the EHL tendon.

The systems as described herein may have alternative configurations to perform a Lapidus procedure that is used to treat a bunion deformity, also known as hallux valgus. In general, the procedure may involve fusing tarsometatarsal (TMT) joint the joint between the first metatarsal bone the medial cuneiform. Surgery includes removing the cartilage surfaces from both bones, correcting the angular deformity, then placing hardware bone plates and anchors in place as needed. Accordingly, embodiments of the present disclosure include a bone fixation system 1010 configured to perform a Lapidus procedure and secure bone segments together includes a bone plate 1100, one or more crossing anchors 1300, at least two bone anchors 1300, 1350, and an optional targeting instrument 1400, as shown in FIGS. 31-44. In some cases, drill guides are used to facilitate placement of the bone plate into the tissue and to guide the drills and/or anchors and other devices to the correct position. In addition, other devices, such as fixation wires, k-wires, fixation pins and like may be used to aid in the targeting and delivery of the bone anchors relative to the bone plate 1100.

Figure 31:
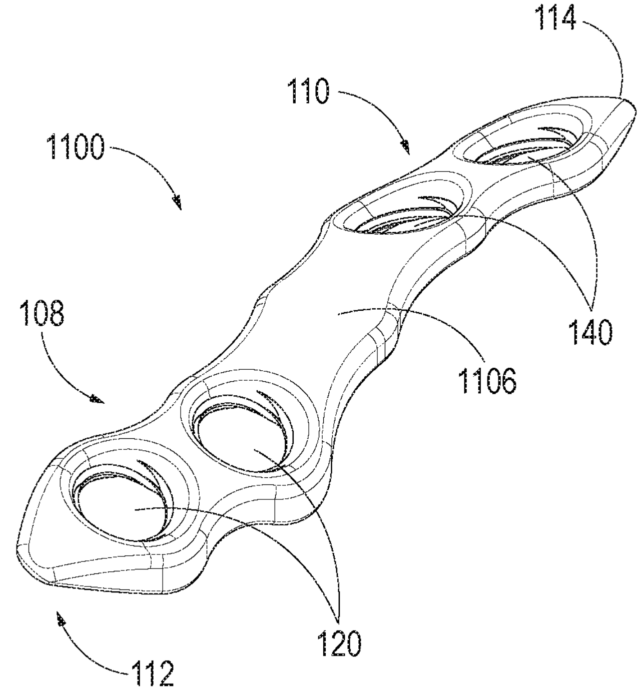
FIG. 31 is a top perspective view of a bone plate used for Lapidus procedure, according to an embodiment of the present disclosure.
Figure 32:
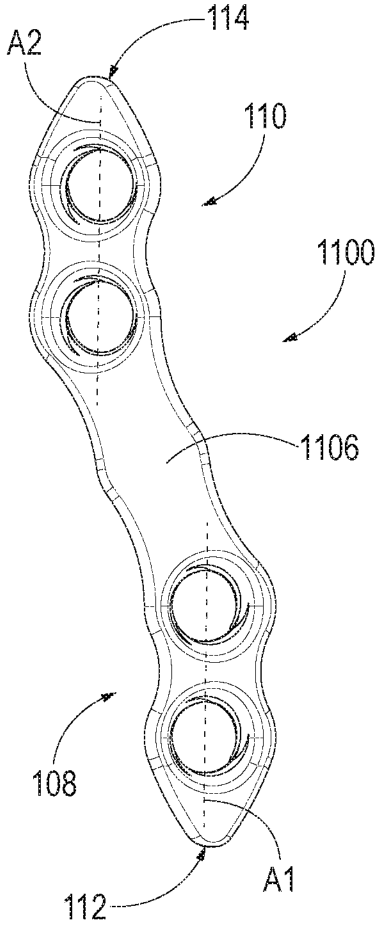
FIG. 32 is a top view of the bone plate used for Lapidus procedure shown in FIG. 31.
Figure 33:
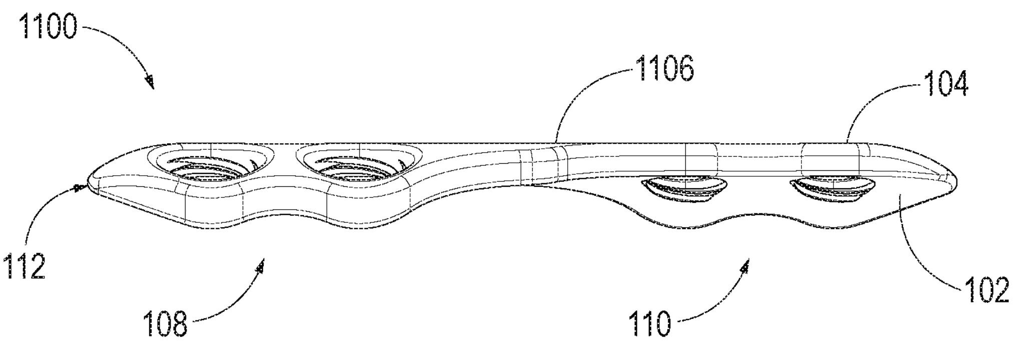
FIG. 33 is a side view of the bone plate used for Lapidus procedure shown in FIG. 31.

Referring to FIGS. 31-33 a bone plate 1100 is shown which is substantially like the bone plate 100 described above and shown in FIGS. 2-6. Accordingly, the same reference numbers are used to identify features of the bone plate that are common to the bone plate 100 and the bone plate 1100. As shown, the bone plate 1100 includes an inferior surface 102, a superior surface 104 opposite the inferior surface 102. The inferior surface of the bone plate 1100 is curved to conform to the anatomy of the foot bone against which it is placed. The superior surface 104 may track the same or substantially similar curvature of the inferior surface 102. The bone plate 1100 includes a central portion (or central bridge 1106) configured to span a joint, a proximal fixation portion 108 extending from and angularly offset with respect to the central bridge 106, and a distal fixation portion 110 extending from and angularly offset with respect to the central bridge 106. The central bridge 106 extends along a bridge axis B1. In the embodiment shown, the central bridge 1106 is longer than the central bridge 106 of the bone plate 100. Otherwise, the bone plates 100 and 1100 are substantially the same.

The bone plate 100 may have a proximal end 112 at the proximal fixation portion 108 that is tapered, and a distal end 114 at the distal fixation portion 110 that is tapered. The tapered proximal and distal ends 112, 114 are configured to guide the bone plate 100 between skin and bone proximate and across joint during insertion to the fixation site. Again, like bone plate 100, for the bone plate 1100, the proximal end may be referred to a leading end of the bone plate 1100 and the distal end may be referred to as the trailing end of the bone plate 1100, depending on direction of insertion. Likewise, the proximal end of the bone plate 1100 may be referred to as the trailing end of the bone plate 1100 and the distal end of the bone plate may be referred to as the leading end of the bone plate. Thus, the two opposed ends may be referred to a proximal, distal, trailing, or leading based on context.

The proximal fixation portion 108 has one or more through-holes 120 that extend from the superior surface 104 to the inferior surface 102. And the distal fixation portion 110 has one or more through-holes 120 that extend from the superior surface 104 to the inferior surface 102. As shown in the figures, the one or more through-holes 120 on the proximal fixation portion are generally aligned along a first axis A1. And the one or more through-holes 120 on the distal fixation portion are generally aligned along a second axis A2. The bone plate 1100 may also include sets of bores (not shown) for receiving wires, such as a k-wires or fixation pines. These bores may be placed between two adjacent through-holes and/or between a through-hole and the proximal and distal ends of the plate, respectively.

The central bridge 1106 offsets the through-holes 120, 140 in proximal and distal fixation portions of the bone plate 100 such that the first axis A1 and the second axis A2 do not intersect. For example, the first axis A1 and the second axis A2 may be parallel. Furthermore, the central bridge 106 extends along the bridge axis B1 and forms oblique angles with the first axis A1 and the second axis A2. These configurations result in a bone plate that can span a fixation site when the bone plate 1100 is implanted.

Figure 34:
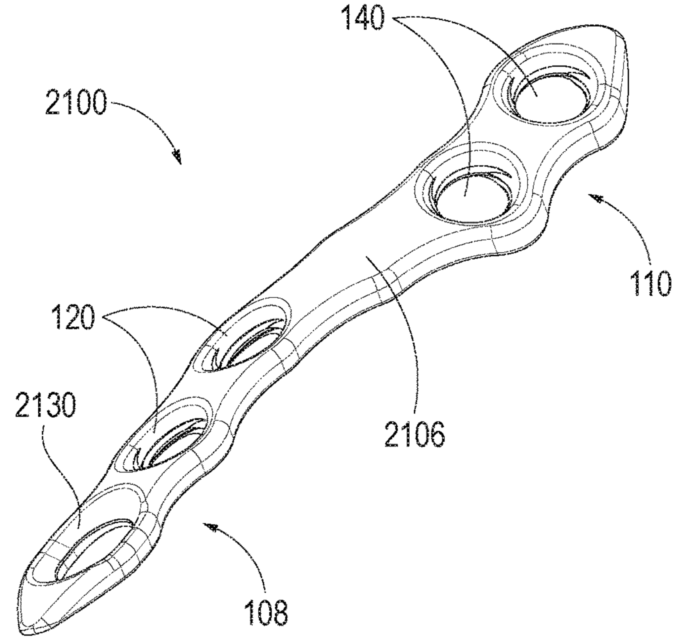
FIG. 34 is a top perspective view of a bone plate used for Lapidus procedure, according to another embodiment of the present disclosure.
Figure 35:
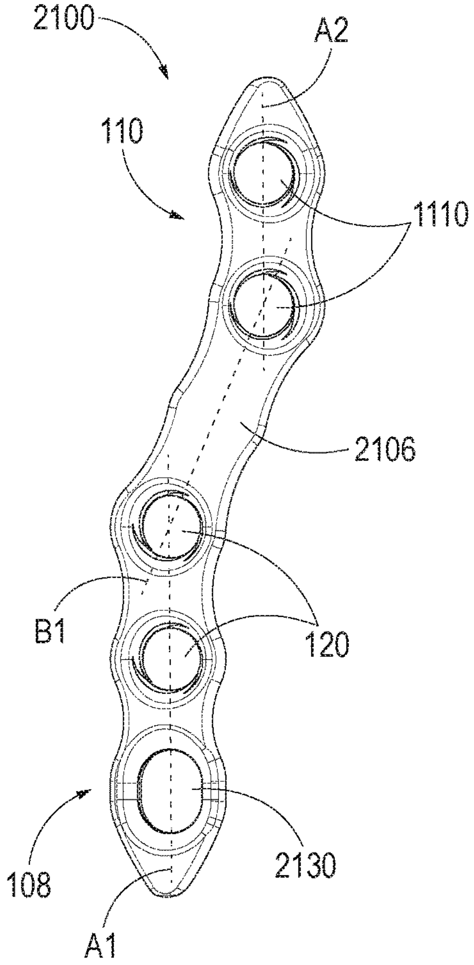
FIG. 35 is a top view of the bone plate used for Lapidus procedure shown in FIG. 34.
Figure 36:
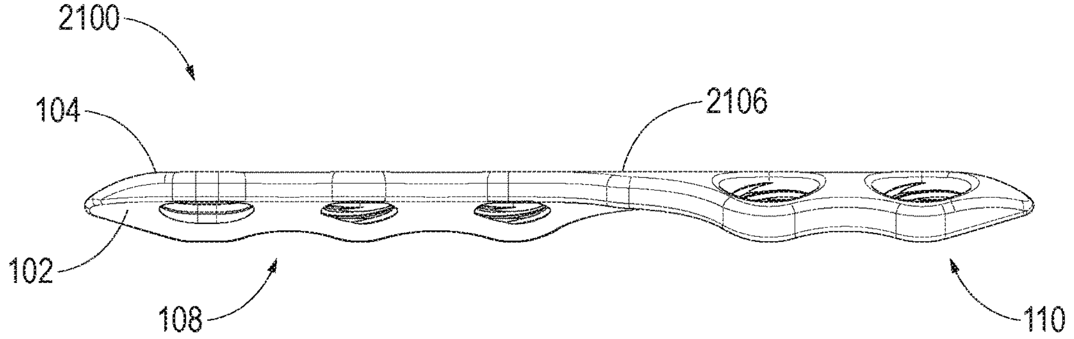
FIG. 36 is a side view of the bone plate used for Lapidus procedure shown in FIG. 34.

FIGS. 34-36 include another embodiment of a bone plate 2100 for use in the bone fixation system 1010. Here, the bone plate 2100 is substantially like the bone plate 100 and bone plate 1100 described above and shown in FIGS. 2-8 and 31-34, respectively. Accordingly, the bone plate 2100 includes a central bridge 2106, a proximal fixation portion 108 with one or more through-holes 120 and a slot 2130, and a distal fixation portion 110 with one or more through-holes 140. In the example shown, the proximal fixation portion 108 of the bone plate 2100 includes two through-holes 120 and a slot 2130 and the distal fixation portion of the bone plate include two through-holes 140. The slot 2130 and through-holes 120 are aligned along axis A1 and the two through-holes 140 are aligned along axis A2. The axes A1 and A2 do not intersect and are angularly offset with respect to axis B1, along which the central bridge 2106 extends.

Figure 37:
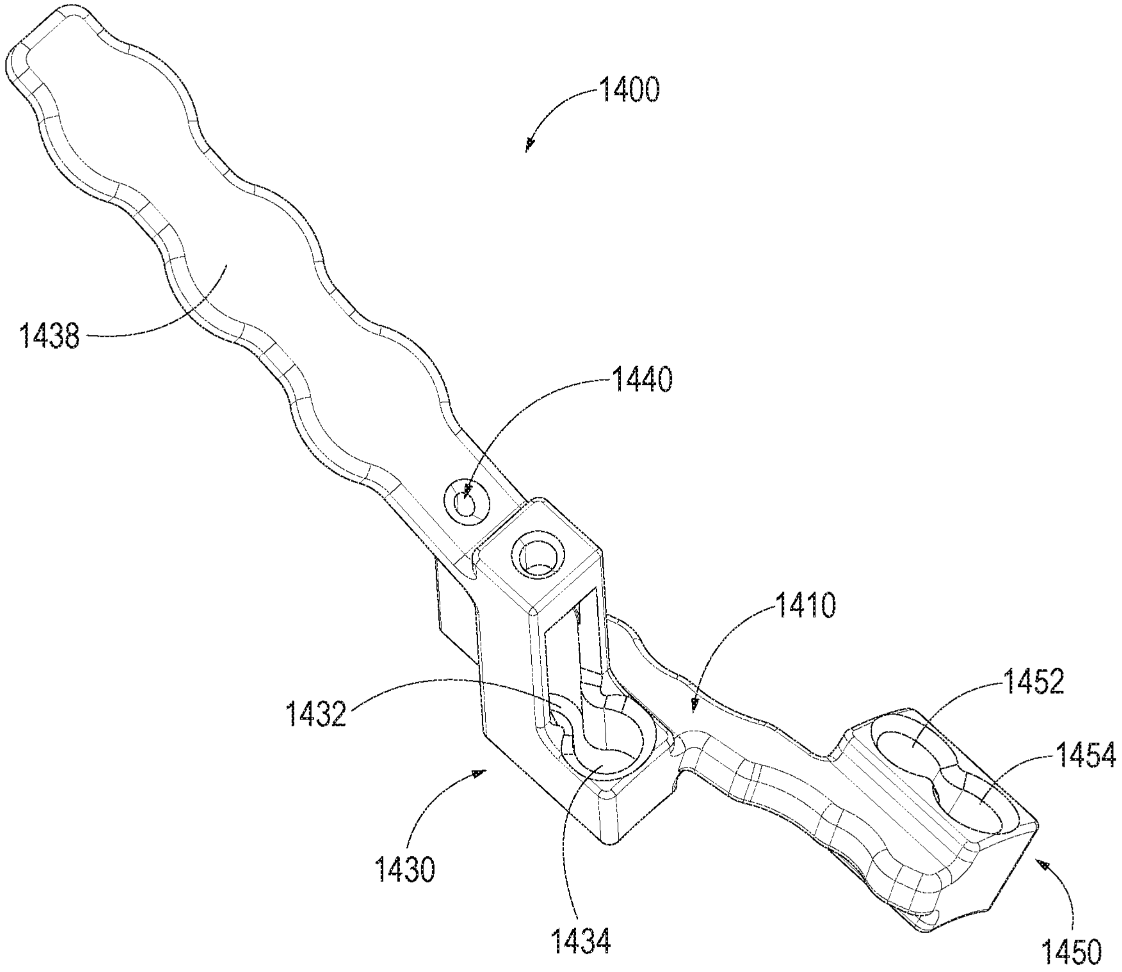
FIG. 37 is a top perspective view of a targeting instrument for a Lapidus procedure according to an embodiment of the present disclosure.
Figure 38:
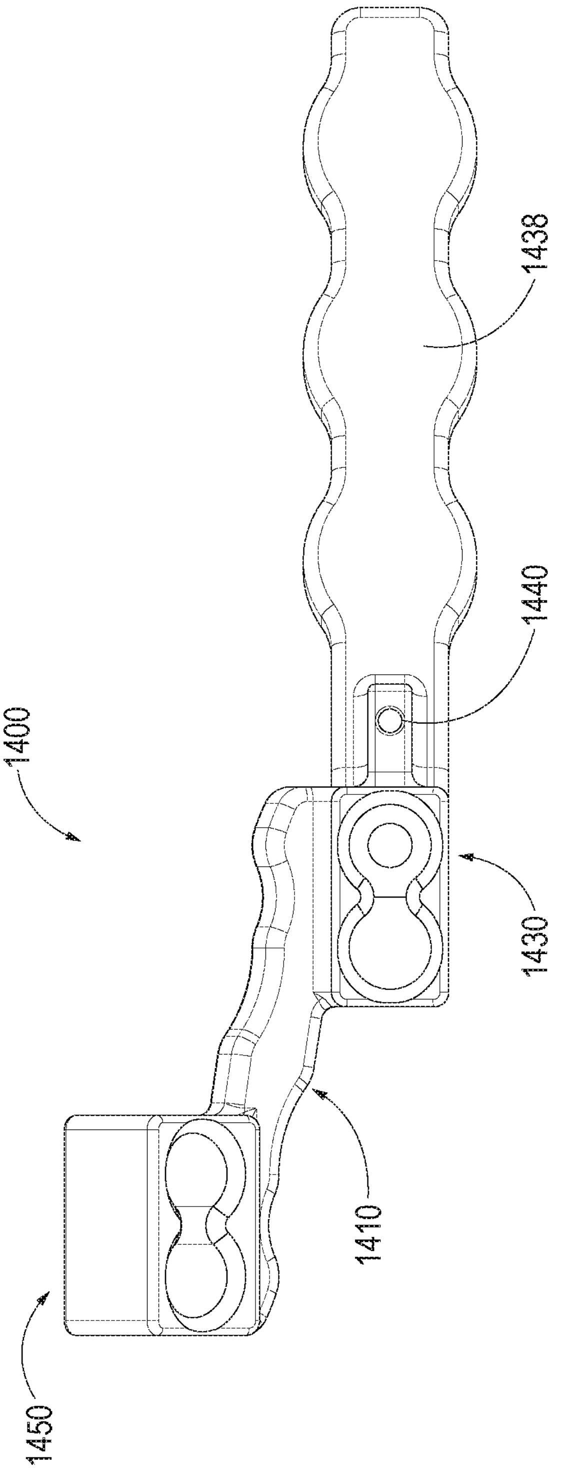
FIG. 38 is a bottom perspective view of the targeting instrument shown in FIG. 37.

Referring to FIGS. 37 and 38, the bone fixation system 1010 includes a targeting instrument 1400 having a platform 1410, a proximal guide body 1430 coupled the platform 1410, and a distal guide body 1450 coupled to the platform 1410 and generally opposite the proximal guide body 1430. In an alternative version, however, the targeting instrument 400 could include a one guide body, such as guide body 1430, thus omitting the distal guide body 1450. Thus, the targeting instrument could include the platform 1410 and one or more guide bodies coupled to the bridge. The platform 1410 includes a platform body with an upper surface 1412 and a lower surface 1414 configured to face tissue and bone plate when in use. In addition, the targeting instrument 1400 also includes a gripping arm 1438 extending from the proximal guide body 1430.

Figure 40:
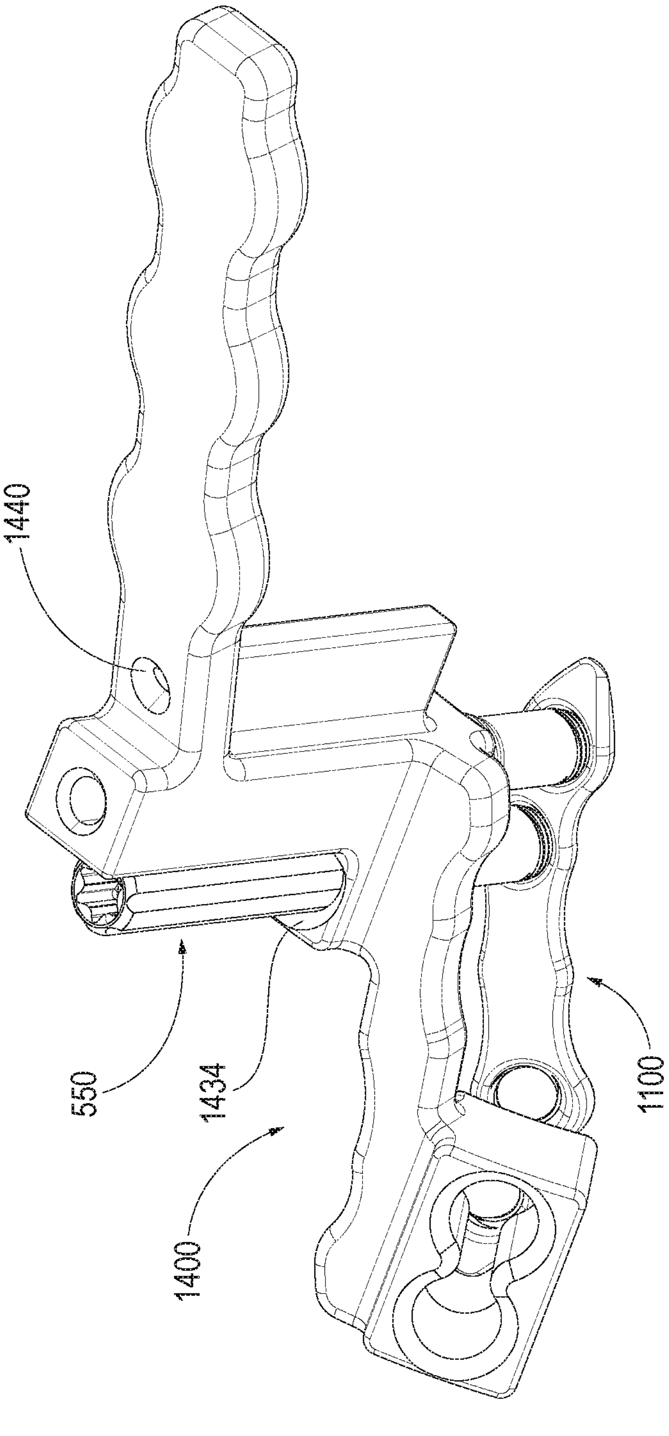
Figure 41:
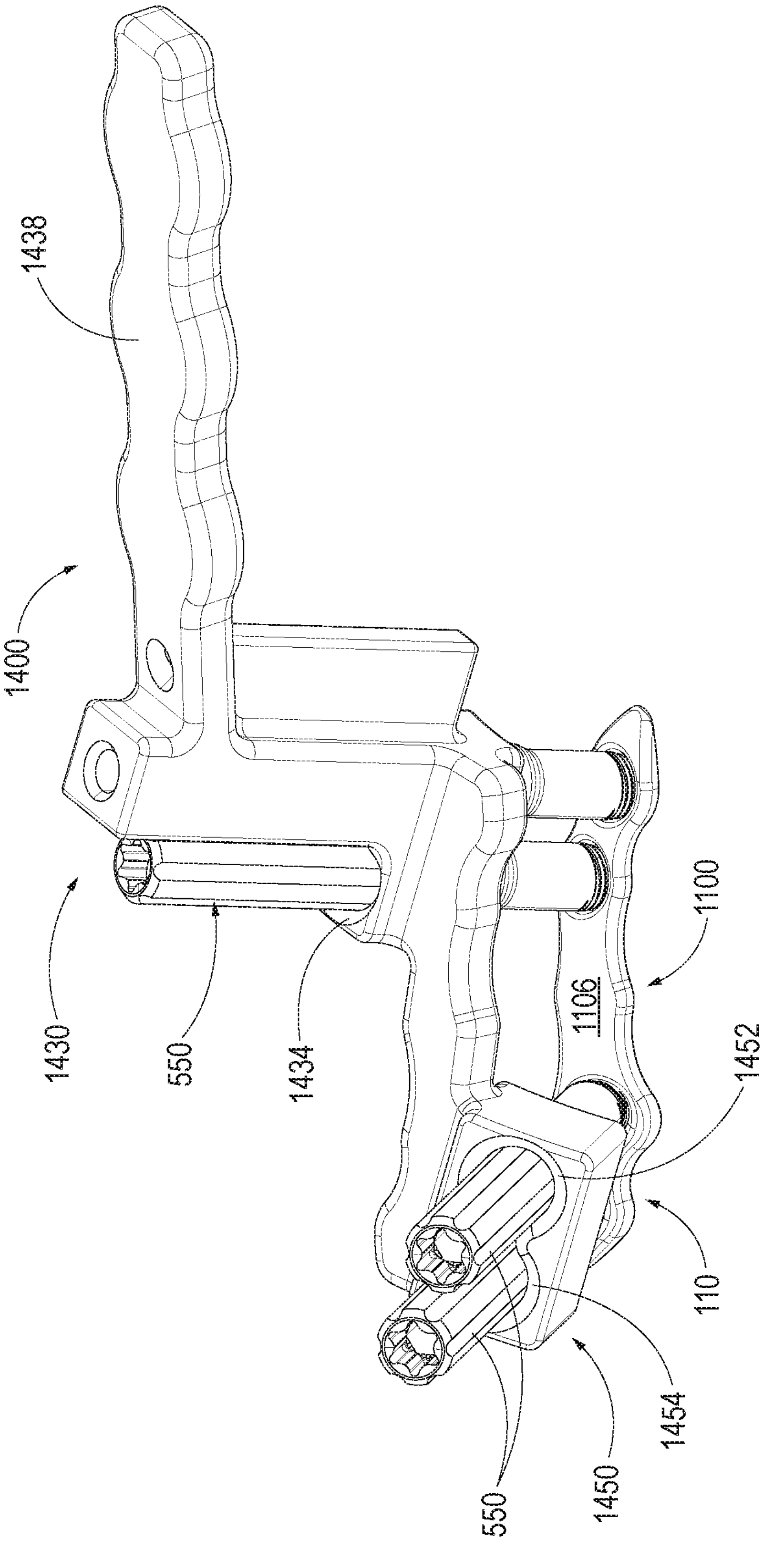

The proximal guide body 1430 has one or more guide channels for receiving one or more drill guides 550, respectively. For example, the proximal guide body 1430 has a first guide 1432 channel (also referred to as proximal guide channel) for receiving a first drill guide 550, and a second guide channel 1434 for receiving a second drill guide 550. The proximal guide channels 1432, 1434 extending along a respective proximal guide axes (not labeled) that are coincident with the axes of the through-holes of the bone plate 100 when coupled together as shown in FIGS. 40 and 41. Each guide channel 1432, 1434 is sized and shaped to permit a bone anchor 300 is pass completely through the respective guide body 1430. The proximal guide body 1430 also includes a shoulder (not shown but like the shoulder 436) configured to contact a proximal-most end of a drill guide to set a distance of the target instrument 1400 relative to the bone plate 1100, 2100. In addition, the targeting instrument 400 also includes a gripping arm 1438 extending from the proximal guide body 1430.

The proximal guide body 1430 also includes a stabilization guide channel 440 configured to receive a wire. The stabilization guide channel 440 has a trajectory along an axis that does not intersect the bone plate 1100 when the targeting instrument 1400 is coupled to the bone plate 1100. In the example shown, the guide channels 1432, 1434 and the stabilization guide channel 1440 may be aligned along a common plane (not shown) that extends perpendicular to the upper surface of the platform 1410.

The distal guide body 1450, when present, also has one or more guide channels for receiving one or more drill guides. As shown, the distal guide body 1450 has a first guide channel 452 for receiving a first drill guide 550, and a second guide channel 1454 for receiving a second drill guide 550. The one or more distal guide channels 1452, 1454 extending along a respective distal guide axes (not shown) that are coincident with the axes of the through-holes of the bone plate 1100 when coupled together as shown in FIGS. 40 and 41. Each guide channel 1452, 1454 is sized and shaped to permit a bone anchor 300 is pass completely through the respective guide body.

The surgical method is illustrated in FIGS. 39-45 and may be described as minimally invasive Lapidus procedure tarsometatarsal (TMT) joint fusion of the first metatarsal bone the medial cuneiform. Initially, the surgeon, or other user, prepares the target location in the joint of a foot. The surgeon begins with forming an incision. After forming an incision, the user may may also include using minimally invasive surgical burrs to cut the bone as needed.

Figure 39:
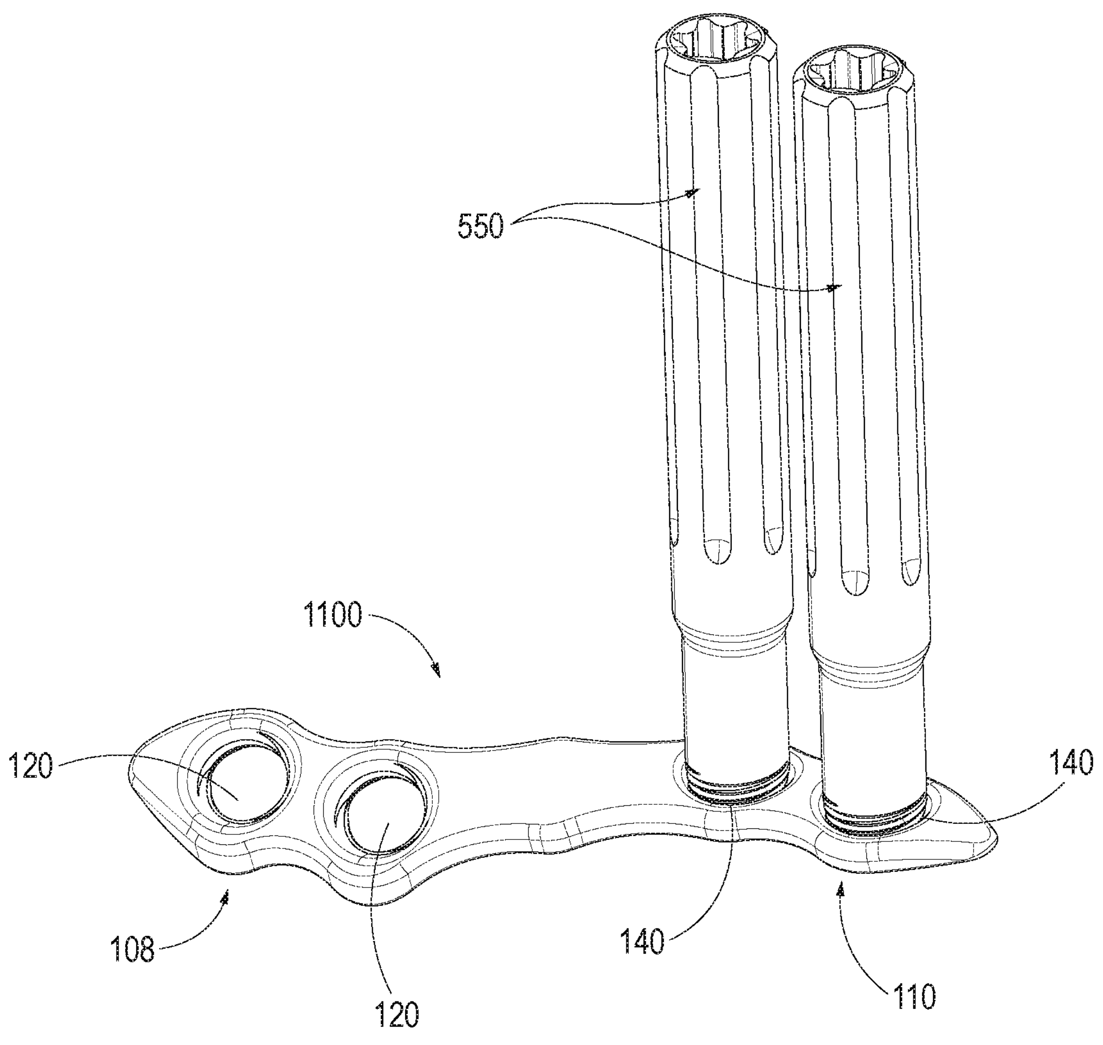
FIGS. 39-43 illustrates a method of using the targeting instrument and arm shown in FIGS. 37-38 to implant a bone fixation system according to another embodiment of the present disclosure.

In the operating environment, a user can insert one or more drill guides 550 into one or more through-holes of in a proximal region of a bone plate 1100. For example, as shown in FIG. 39, a first proximal drill guide 550 is threadably engaged with a first through-hole 120 in a proximal region of the bone plate 1100 and a second proximal drill guide 550 is threadably engaged with a second through-hole 120 in the proximal region of the bone plate 1100. In some instances, the user can use the drill guide-bone plate assembly to insert the bone plate 1100 into position across the desired bone target location. More specifically, the user can hold the drill guides and an insert a first end of the bone plate through the incision until the one or more through-holes of the proximal region of the bone plate are in position. In other instances, the surgeon may use the targeting instrument 1400.

Turning to FIG. 41, the user can couple the targeting instrument 400 by inserting the proximal drill guides 550 into the proximal channels 1432, 1434 of the proximal guide body 1430 of the target instrument 1400. Like the targeting instrument 400 shown in FIGS. 14A, 14B and described above, the target instrument 1400 slides along the drill guides 550 until the proximal surface of the drill guides abuts the shoulder of the proximal guide body 1430 of the targeting instrument 1400. This, in turns, sets the distance of the targeting instrument 1400 relative to the bone plate 2100. Next, the user can position the bone plate 1100 into the target location of the joint with the targeting instrument 1400 and drill guides 550 coupled to the bone plate 1100. This involves positioning an end of the bone plate 1100 through the incision on the proximal side of the joint or target location if the bone plate is not intended to span a joint. Or it could be placed on the distal side of the joint first. Next, a stabilizing wire may be inserted through a wire channel 1440 of the targeting instrument 1400, which in turns, holds the assembly of the targeting instrument 1400 and bone plate 1100 in place relative to the bone. The user can form a separate second incision in the tissue at a location that is distal (or proximal as needed) with respect to the proximal region of the bone plate 1100. This provides access so that the two anchors 300 can be placed in the intended through-holes of the bone plate 1100.

In FIG. 41, the user can insert one or more distal drill guides 550 into one or more distal channels 1452, 1454 of targeting instrument 1400. For example, a first distal drill guide 550 is inserted through the first distal guide channel 1452 of the targeting instrument 1400 and a second distal drill guide 550 is inserted through the second distal guide channel 1454 of the targeting instrument 1400. Using a drill, the user can then drill holes in the target location of the bone through the distal drill guides 550. Once the holes are formed in the bone, the distal drill guides 550 are removed, as shown in FIG. 42.

Figure 42:
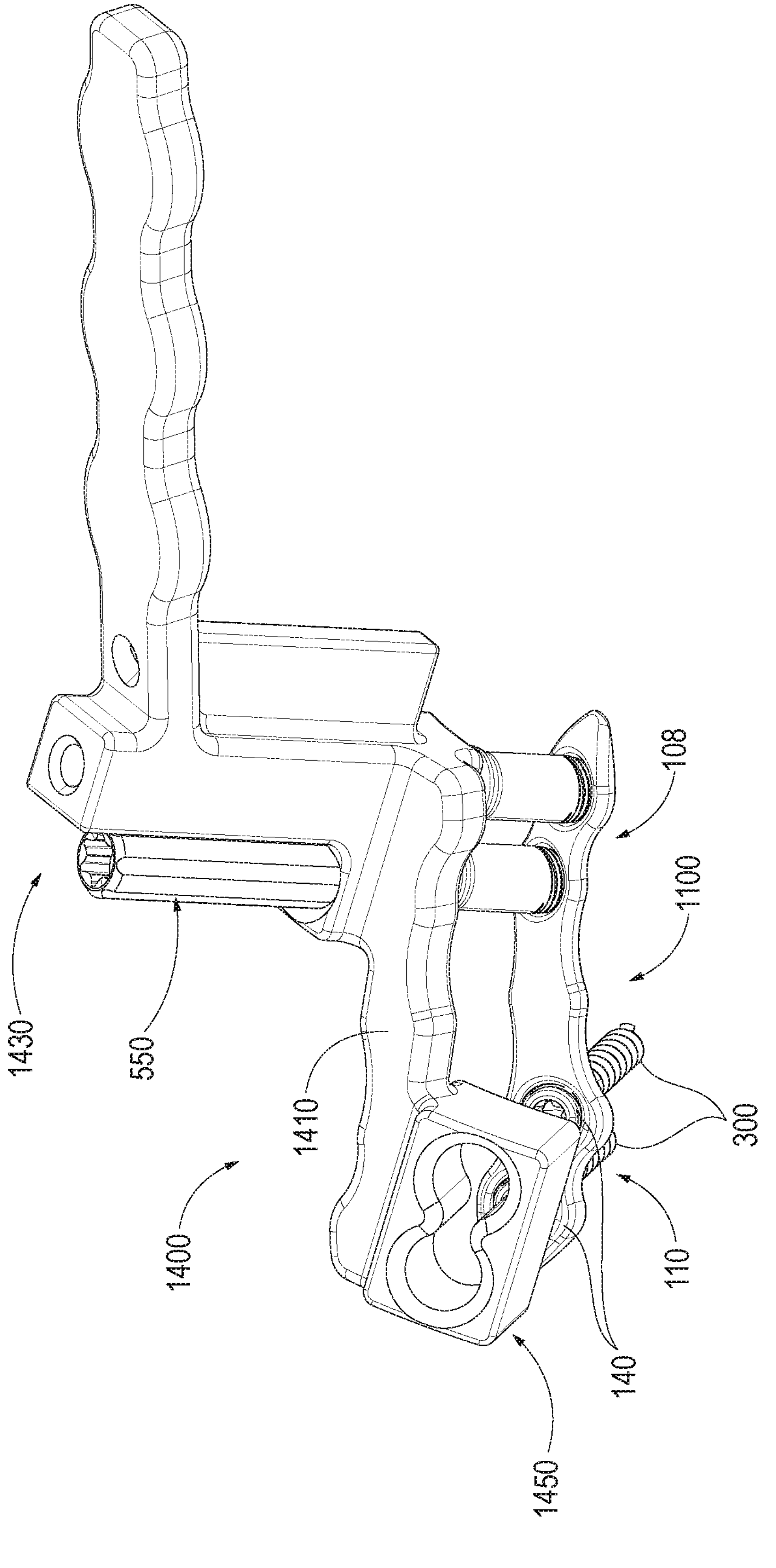

Continuing with FIG. 42, the user can insert one or more bone anchors 300 into the bone through the one or more through-holes 140 in a distal region of the bone plate 1100. As shown, a first distal bone anchor 300 is inserted into a first through-hole 140 of the bone plate 1100 (in the distal portion), and a second distal bone anchor 300 is inserted in the second through-hole 140 of the bone plate 100 (in the distal portion). Here, one bone anchor 300 could be a locking anchor and the other bone anchor could be a compression anchor. Alternatively, both anchors could be the same type anchors, e.g. two locking anchors or two compression anchors.

Figure 43:
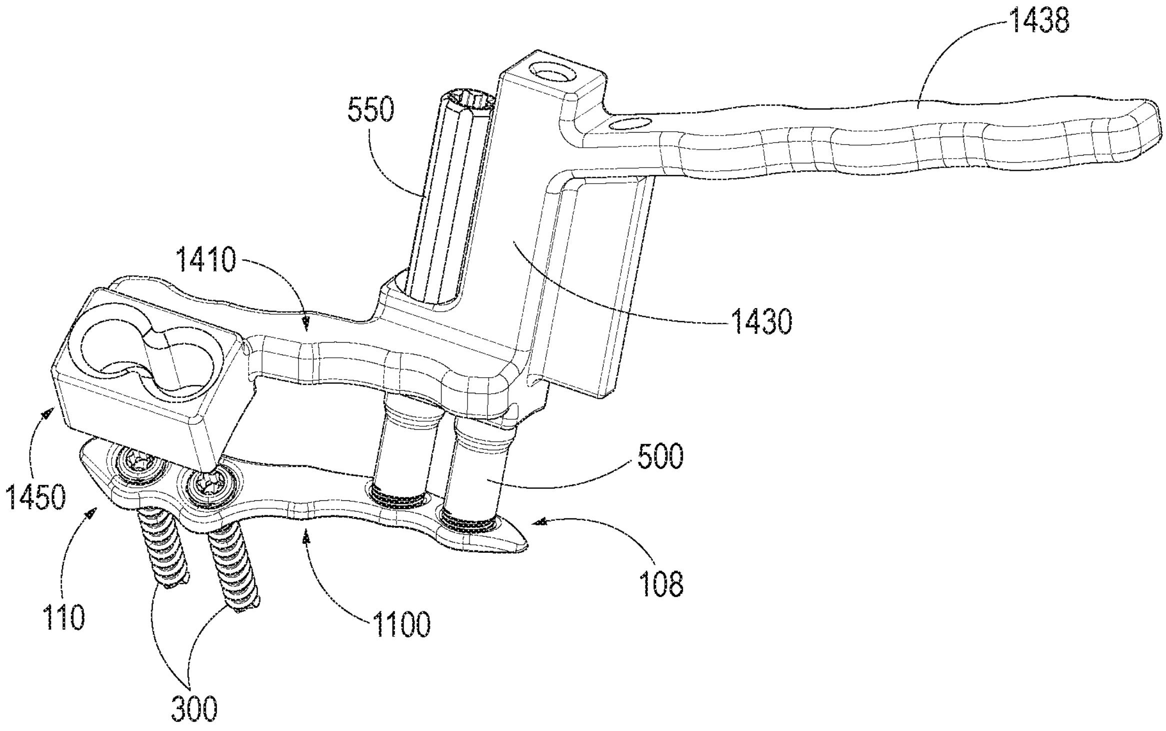
Figure 44:
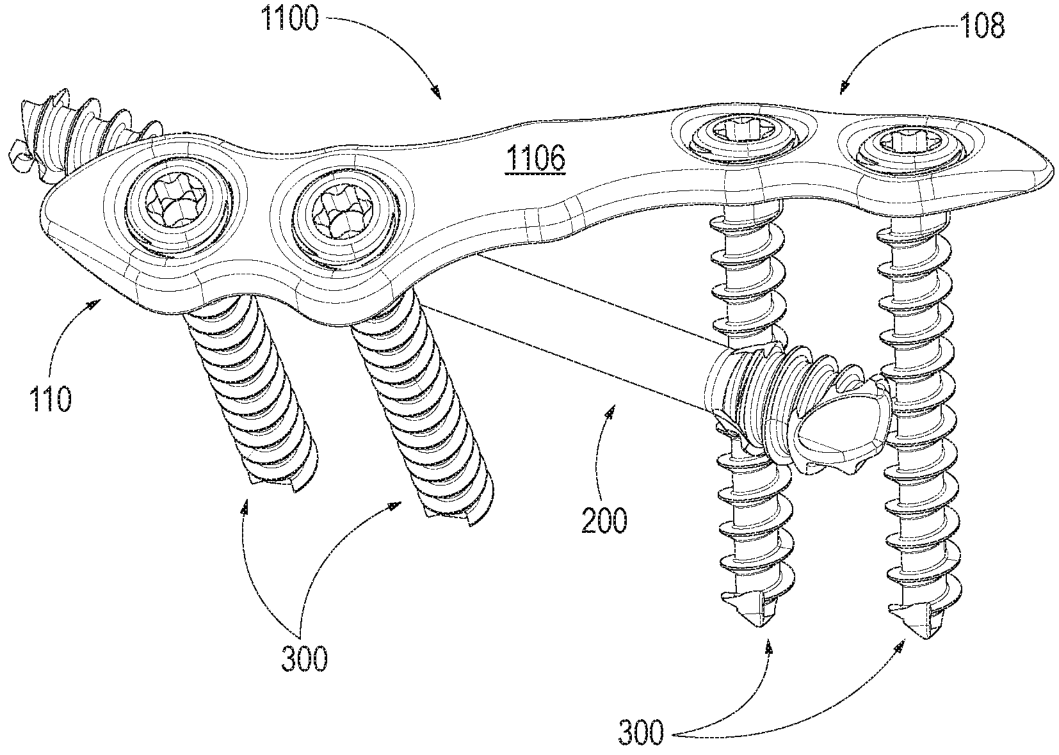
FIG. 44 illustrates a perspective view of the bone plate and bone anchors, and a crossing anchor in an implanted state with the bone removed for illustrative purposes according to another embodiment of the present disclosure.

In FIG. 43, one the anchors 300 are implanted through the region 110 of the bone plate 1100, the targeting instrument 1400 can be removed from the drill guides 550 (which remain coupled to the bone plate 1100 at the proximal region 108. The drill guides 550 can then be removed from the bone plate 1100. At this point, the anchors 300 can be inserted into the through-holes 120 and into the target bone. Here, one bone anchor could be a locking anchor, and the other bone anchor could be a compression anchor. Alternatively, both anchors could be the same type. In some instances, a crossing anchor 200 (as shown in FIG. 44) may be inserted across the joint before the anchors 300 are inserted through the through-holes 120 of the bone plate 1100. The result is a set of anchors 300 engaged with a proximal portion 108 of the bone plate 1100, a set of anchors 300 engaged with the distal portion 110 of the bone plate 1100, and a crossing anchor 200 spanning the joint and in positioned between the shafts of all the bone anchors (without contact) and inferior to the bone plate 1100 (without contacting the bone plate 100), as shown in FIG. 44. The crossing anchor 200 is placed between the implanted bone anchors and inferior to the bone plate 1100. In other words, the crossing anchor 200, once implanted, does not contact or touch any bone anchor or any part of the bone plate 1100.

Figure 45:
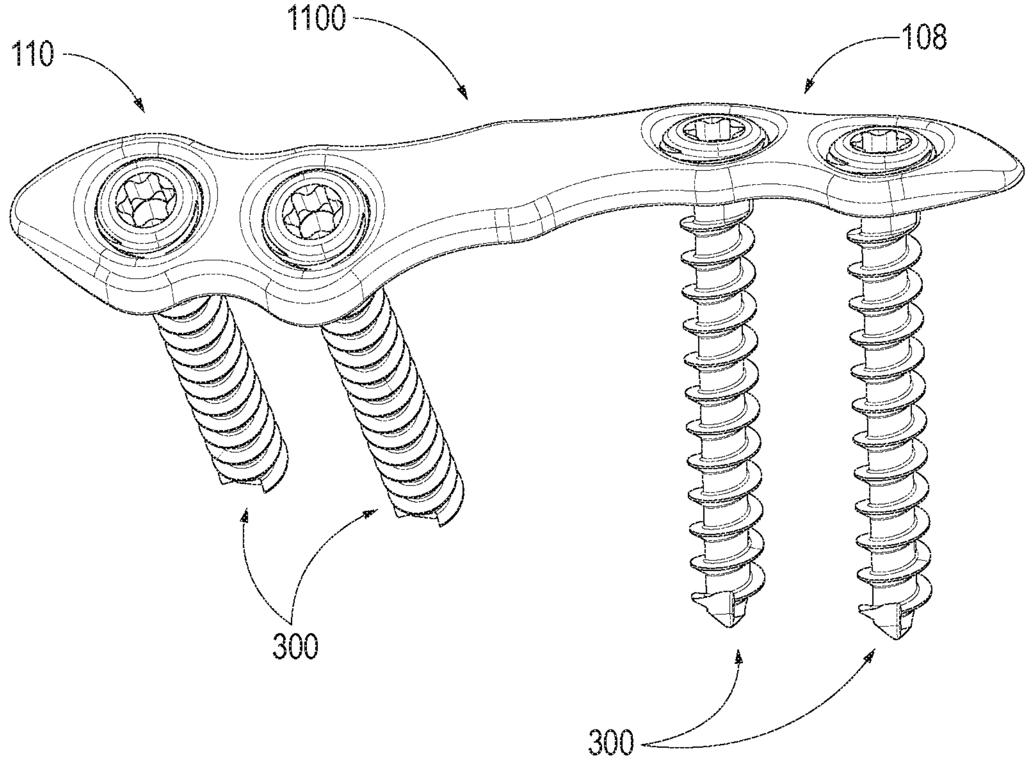
FIG. 45 illustrates a perspective view of the bone plate and bone anchors, without use of a crossing anchor, in an implanted state with the bone removed for illustrative purposes according to another embodiment of the present disclosure.

FIG. 45 illustrates an alternative embodiment where two bone anchors 300 engaged with a proximal portion 108 of the bone plate 1100, two bone anchors 300 engaged with the distal portion 110 of the bone plate 1100 but no crossing anchor is used.

The surgical methods described above are for metatarsal phalangeal (MTP) joint fusion or the Lapidus procedure using a combination of drill guides, bone plate, bone anchors, and a targeting instrument. However the bone plate may be positioned without the need for the targeting instrument and could be used for procedures in other parts of the body, such as extremity bones. Here, the method includes forming a first incision in tissue near a first bone segment of a foot bone, finger bone or other extremity bone. Next, a user may couple one or more drill guides to a trailing end of a bone plate. Here, the trailing end of the bone plate includes one or more through-holes aligned with the one or more drill guides. The method includes inserting, with the one or more drill guides coupled to the trailing end of the bone plate, a leading end of a bone plate into the first incision toward a second bone segment. Here, the leading end includes one or more through-holes. The method also includes positioning the bone plate in the incision so that a central bridge of the bone plate spans the first bone segment and a second bone segment. In this case, the trailing end is located adjacent the first bone segment, and the leading end is located adjacent to the second bone segment. The method includes implanting one or more first bone anchors into one or more through-holes at the trailing end of the bone plate and into the first bone segment. Next, the method includes forming a second incision near the where the leading end is located near the second bone segment. Then, the user can implant one or more second bone anchors through the second incision into the one or more through-holes at the leading end of the bone plate into the second bone segment. The resulting construct is illustrated in FIGS. 27-40 and 43-45.

Embodiments of the present disclosure may further include examples of bone fixation systems and methods as described below.

In a first example, there is a system for fixation or fusion of a joint located between bone segments in a foot bone. The system includes a targeting instrument having a platform, a guide body having one or more guide channels, a stabilizing guide channel for receiving a stabilizing wire, and the one or more guide channels have a size and shape configured to receive one or more drill guides. The system may also include an anchor targeter having a base sized and shaped rotatably engage the platform, an aiming arm extending and curving from the base, an aiming body at a terminal end of the arm and aiming channel that extends through entirely through the aiming body. The aiming channel extends along a targeting axis that is inferior to and does not intersect the platform. The anchor targeter is configured to rotate relative to the platform to align targeting axis with a desired anchor trajectory.

In a second example, there is system for fixation or fusion of a joint located between bone segments in a foot bone. The system includes a targeting instrument having a platform, a guide body having one or more guide channels, a stabilizing guide channel for receiving a stabilizing wire. The one or more guide channels have a size and shape configured to receive one or more drill guides. The system includes an anchor targeter having a base sized and shaped engage the platform, an aiming arm extending and curving from the base, an aiming body at a terminal end of the arm, and an aiming channel that extends through entirely through the aiming body. The aiming channel extends along a targeting axis that is inferior to and does not intersect the platform. The anchor targeter is configured to align targeting axis with a desired anchor trajectory.

In the first or second example, the anchor targeter is engageable to the platform such that it does not rotate In any example described above, the guide body is a proximal guide body having one or more proximal guide channels, and the targeting instrument further comprises a distal guide body having one or more distal guide channels.

In any example described above, the one or more proximal guide channels extend along a proximal guide axis, and the one or more guide channels extend along a respective distal guide axis that is angled with respect to the proximal guide axis.

In any example described above, each guide channel is sized and shaped to permit a bone anchor is pass completely therethrough.

In any example described above, the stabilization guide channel has a trajectory along an axis that does not intersect a bone plate when the targeting instrument is coupled to the bone plate.

In any example described above, the targeting instrument includes one or more first engagement elements, and the anchor targeting include one or more second engagement elements configured to engage the first engagement elements.

In any example described above, the one or more first engagement elements comprise a pivot post extending from the platform, a guide post extending from the platform and spaced toward an outer edge of the platform, and a curved ridge extending from the platform, wherein the curved ridge arcs relative to the pivot post.

In any example described above the one or more second engagement elements are on the base of the anchor targeter and include a bore configured to couple to the pivot post, a first slot that receives the curved ridge, and a second slot that receives the guide post, wherein AI rotates about the pivot post to adjust the trajectory of the aiming body and the targeting axis.

In any example described above, the one or more guide bodies include a shoulder configured to contact a proximal-most end of a drill guide to set a distance of the target instrument relative to a bone plate when the targeting instrument is coupled to the bone plate.

In any example described above, the system further includes one or more drill guides, wherein the one or more drill guides includes a tip configured to threadably engage holes in a bone plate, and a cannulation that extends from the tip through the drill guide.

In a third example, there includes a system for fixation or fusion of a joint located between bone segments in a foot bone. The system includes one or more drill guides. The one or more drill guides includes a tip configured to threadably engage holes in a bone plate, and a cannulation that extends from the tip through the drill guide. The system includes an anchor targeter including a base configured to attach directly to one more drill guides, an aiming arm extending and curving from the base, an aiming body at a terminal end of the arm, and an aiming channel that extends through entirely through the aiming body. The aiming channel extends along a targeting axis that is inferior to and does not intersect the platform and the anchor targeter is configured to align targeting axis with a desired anchor trajectory.

In the third example, the system further comprises a targeting instrument having a platform, a guide body having one or more guide channels, a stabilizing guide channel for receiving a stabilizing wire, wherein the one or more guide channels have a size and shape configured to receive one or more drill guides.

Any of the examples described above can be used in combination with the third example and examples that depend therefrom.

In any of the examples described above, the system includes a bone plate having one or more proximal through-holes and one or more distal through-holes spaced apart from the one or more proximal through-holes, one or more proximal bone anchors configured to be inserted into the one or more proximal through-holes of the bone plate, one or more distal bone anchors configured to be inserted into the one or more distal through-holes of the bone plate, and a crossing anchor having a shaft with a proximal end and a distal end spaced from the proximal end along a central axis. The proximal end has a proximal beveled surface that is angled with respect to the central axis. The crossing anchor is configured to span the joint and be spaced from the inferior surface of the bone plate and each shaft of the one or more proximal bone anchor and the one or more distal bone anchors when the bone plate and proximal and distal bone anchors are implanted into the bone segments of the foot bone.

In a fourth example, there includes a system for fixation or fusion of bone segments in an extremity bone. The system includes a bone plate having one or more proximal through-holes and one or more distal through-holes spaced apart from the one or more proximal through-holes. The bone plate is configured so that when the bone plate is implanted across a first and second bone segments, the one or more proximal through-holes are positioned adjacent the first bone segment and the one or more distal through-holes are positioned on the second bone segment. The system includes one or more proximal bone anchors configured to be inserted into the one or more proximal through-holes of the bone plate into the first bone segment when the bone plate is in positioned adjacent the extremity bone, one or more distal bone anchors configured to be inserted into the one or more distal through-holes of the bone plate when the bone plate is in positioned adjacent the extremity bone, and a crossing anchor having a shaft with a proximal end and a distal end spaced from the proximal end along a central axis, the proximal end having a proximal beveled surface that is angled with respect to the central axis to sit substantially flush with a bone surface when implanted in one or both of the first bone segment and the second bone segment. The crossing anchor is configured to span the first and second bone segments and be spaced from the bone plate, the shafts of the one or more proximal and the shaft of the one or more distal bone anchors when the bone plate and the one or more proximal bone anchors and the one or more distal bone anchors are implanted into the respective bone segments of the extremity bone.

In the fourth example, the bone plate is configured so that when the bone plate is implanted across a joint, the one or more proximal through-holes are positioned on one side of an extensor hallucis longus (EHL) tendon and the one or more distal through-holes are positioned on an other side of the EHL tendon. The crossing anchor is configured to span a joint and be spaced from the bone plate, the EHL tendon, and the one or more proximal and the one or more distal bone anchors when the bone plate and the one or more proximal bone anchors and the one or more distal bone anchors are implanted into the bone segments of the extremity bone.

In the fourth example, wherein the bone plate is configured so that when the bone plate is implanted, the one or more proximal through-holes are positioned on a first metatarsal and the one or more distal through-holes are positioned on a first cuneiform bone. The crossing anchor is configured to be spaced from the bone plate, the shaft of the one or more proximal bone anchors and the shaft of one or more distal bone anchors when the bone plate and the one or more proximal bone anchors and the one or more distal bone anchors are implanted into the bone segments of the extremity bone.

In the fourth example, the bone plate has a central bridge, a proximal fixation portion extending from and angularly offset with respect to the central bridge, and a distal fixation portion extending from and angularly offset with respect to the central bridge. The proximal fixation portion include the one or more proximal through-holes, and the distal fixation portion includes the one or more distal through-holes.

In the fourth example, the one or more proximal through-holes are aligned along a first axis, and the one or more distal through-holes are aligned along a second axis. The first axis does not intersect the second axis so that the one or more proximal through-holes and the one or more distal through-holes are offset. In this example, the bone plate includes an elongated slot aligned along the first axis or the second axis.

In the fourth example, the shaft of the crossing anchor has a proximal region that is threaded, a distal region that is threaded, and a central portion located between the proximal region and the distal region that is not threaded.

In the fourth example, the system includes one or more drill guides, wherein the one or more drill guides includes a tip configured to couple to either of the one or more proximal through-holes and the one or more distal through-holes in the bone plate, and a cannulation that extends from the tip through the drill guide.

In a fifth example, there is a system for fixation or fusion of bone segments in an extremity bone. The system includes one or more drill guides with the one or more drill guides having a tip configured to be coupled to one or more through-holes in a bone plate and a cannulation that extends from the tip through the drill guide. The system includes a targeting instrument having a platform and a guide body and a stabilizing guide channel for receiving a stabilizing wire.

The guide body has one or more guide channels with a size and shape configured to receive the one or more drill guides.

In the firth example, the system further includes an anchor targeter having a base sized and shaped to rotatably engage the platform, an aiming arm extending and curving from the base, an aiming body at a terminal end of the aiming arm, and an aiming channel that extends through the aiming body. The aiming channel extends along a targeting axis that is inferior to and does not intersect the platform. The anchor targeter is configured to rotate relative to the platform to align the targeting axis with a desired anchor trajectory.

In the fifth example, the anchor targeter is engageable to the platform such that it does not rotate.

In the fifth example, the guide body is a proximal guide body having one or more proximal guide channels, and the targeting instrument further comprises a distal guide body having one or more distal guide channels.

In the fifth example, the one or more proximal guide channels extend along a proximal guide axis, and the one or more guide channels extend along a respective distal guide axis that is angled with respect to the proximal guide axis.

In the fifth example, the one more guide channels of the guide body are sized and shaped to permit a bone anchor is pass completely therethrough.

In the fifth example, the stabilization guide channel has a trajectory along an axis that does not intersect a bone plate when the targeting instrument is coupled to the bone plate.

In the fifth example, the targeting instrument includes one or more first engagement elements, and the anchor targeter include one or more second engagement elements configured to engage the first engagement elements.

In the fifth example, the one or more first engagement elements comprise a pivot post extending from the platform, a guide post extending from the platform and spaced toward an outer edge of the platform, and a curved ridge extending from the platform, wherein the curved ridge curves relative to the pivot post. Furthermore, the one or more second engagement elements are on the base of the anchor targeter and include a bore configured to couple to the pivot post, a first slot that receives the curved ridge, and a second slot that receives the guide post, wherein the anchor targeter rotates about the pivot post to adjust a trajectory of the aiming body and the targeting axis.

In the fifth example, the guide body includes a shoulder configured to contact a proximal-most end of a drill guide to set a distance of the target instrument relative to a bone plate when the targeting instrument is coupled to the bone plate.

In the fifth example, the system further includes a bone plate having one or more proximal through-holes configured to be positioned adjacent a first bone segment, and one or more distal through-holes spaced apart from the one or more proximal through-holes and configured to be positioned adjacent a second bone segment, one or more proximal bone anchors configured to be inserted into the one or more proximal through-holes of the bone plate and into the first bone segment when the bone plate is in position adjacent the first bone segment, one or more distal bone anchors configured to be inserted into the one or more distal through-holes of the bone plate and into the second bone segment when the bone plate is in position adjacent the second bone segment and a crossing anchor having a shaft with a proximal end and a distal end spaced from the proximal end along a central axis, wherein proximal end has a proximal beveled surface that is angled with respect to the central axis so that it sits flush with a surface of either the first bone segment or the second bone segment. The crossing anchor is configured to span the first and second bone segments and be spaced from an inferior surface of the bone plate and a shaft of the one or more proximal bone anchors and a shaft of the one or more distal bone anchors when the bone plate and proximal and distal bone anchors are implanted into the bone segments.

In a sixth example, there is a method that includes inserting one or more drill guides into one or more first through-holes a bone plate, coupling a targeting instrument to one or more drill guides such that the targeting instrument is positioned a set distance relative to the bone plate, inserting one or more first bone anchors into a target location of the bone segments through the one or more drill guides and the one or more through-holes of the bone plate, coupling a base of an anchor targeter to a platform of the targeting instrument, positioning a crossing-anchor across a joint along the targeting axis and inferior to the bone plate and platform, and inserting one or more second bone anchors through one or more second through-holes in the bone plate.

In the sixth example, the method includes, before positioning the crossing anchor across the joint, rotating the anchor targeter relative to the target instrument so that an aiming channel of the anchor targeter aligns a targeting axis with a desired anchor trajectory.

In a sixth example, a method includes inserting one or more drill guides into one or more proximal through-holes in a proximal region of a bone plate, coupling a targeting instrument to one or more proximal drill guides such that the targeting instrument is positioned a set distance relative to the bone plate, positioning the bone plate into a target location of a joint with the targeting instrument and drill guides coupled to the bone plate, inserting one or more distal drill guides into one or more distal channels of the targeting instrument, inserting one or more distal bone anchors into the target location of the bone segments through the one or more through-holes in a distal region of the bone plate, coupling a base of an anchor targeter to a platform of the targeting instrument, rotating the anchor targeter relative to the target instrument so that an aiming channel of the anchor targeter aligns a targeting axis with a desired anchor trajectory, inserting a wire across through the aiming channel of the joint in a region inferior to the bone plate, removing an arm and an aiming body of the anchor targeter from a distal end of the wire, positioning a crossing anchor over the distal end of the wire to compress the joint, removing the wire from a cannulation of the crossing anchor, inserting one or more proximal bone anchors through the one or more through-holes in the proximal region of the bone plate, and removing the targeting instrument and anchor targeter.

In the sixth example, the method also includes before positioning the crossing anchor across the joint, removing an arm and an aiming body from the anchor targeter while leaving the base coupled to the platform.

Wherever possible, the same or like reference numbers are used throughout the drawings to refer to the same or like features. It should be noted that the drawings are in simplified schematic form and are not drawn to precise scale. Certain terminology used in the description is for convenience only and is not limiting. Directional terms such as top, bottom, left, right, above, below and diagonal, are used with respect to the accompanying drawings. The term "distal" shall mean away from the center of a body. The term "proximal" shall mean closer towards the center of a body and/or away from the "distal" end. The words "inwardly" and "outwardly" refer to directions toward and away from, respectively, the geometric center of the identified element and designated parts thereof. Such directional terms used in conjunction with the following description of the drawings should not be construed to limit the scope of the present disclosure in any manner not explicitly set forth. Additionally, the term "a," as used in the specification, means "at least one." The terminology includes the words above specifically mentioned, derivatives thereof, and words of similar import.

"Substantially" as used herein shall mean considerable in extent, largely but not wholly that which is specified, or an appropriate variation therefrom as is acceptable within the field of art. "Exemplary" as used herein shall mean serving as an example.

Furthermore, the described features, advantages and characteristics of exemplary embodiments may be combined in any suitable manner in one or more embodiments. One skilled in the art will recognize, considering the description herein, that the exemplary embodiments can be practiced without one or more of the specific features or advantages of a particular embodiment. In other instances, additional features and advantages may be recognized in certain embodiments that may not be present in all embodiments of the present disclosure.

While the disclosure is described herein, using a limited number of embodiments, these specific embodiments are not intended to limit the scope of the disclosure as otherwise described and claimed herein. The precise arrangement of various elements and order of the steps of articles and methods described herein are not to be considered limiting. For instance, although the steps of the methods are described with reference to sequential series of reference signs and progression of the blocks in the figures, the method can be implemented in an order as desired.

The invention claimed is:

1. A method, comprising:

forming a first incision near a first foot bone segment on a first side of a joint;

forming a second incision near a second foot bone segment on a second side of the joint;

inserting a bone plate into the first incision toward the second foot bone segment;

positioning the bone plate so that the bone plate spans the joint with a first through-hole of the bone plate adjacent to the first foot bone segment and a second through-hole of the bone plate adjacent to the second foot bone segment;

implanting a first bone anchor through the first incision into the first through-hole of the bone plate and the first foot bone segment; and implanting a second bone anchor through the second incision into the second through-hole of the bone plate and the second foot bone segment.

2. The method according to claim 1, further comprising coupling one or more drill guides to a bone plate at one or more through-holes at a trailing end of the bone plate.

3. The method according to claim 2, further comprising, before implanting the one or more first bone anchors into the first through-hole at the trailing end of the bone plate, removing the one or more drill guides from the trailing end of the bone plate.

4. The method according to claim 1, wherein positioning the bone plate in the first incision so that the bone plate spans the first foot bone segment and the second foot bone segment further comprises positioning the bone plate so that a leading end of the bone plate is adjacent the second foot bone segment, a trailing end is adjacent the first foot bone segment and a central bridge of the bone plate spans the joint and the first and second foot bone segments, wherein the leading end and trailing end are angularly offset with respect to the central bridge of the bone plate.

5. The method according to claim 1, further comprising implanting one or more crossing anchors inferior to the bone plate and between shafts of the first bone anchor and the second bone anchor.

6. The method according to claim 5, wherein implanting the one or more crossing anchors occurs after implanting the second bone anchor into the second through-hole at a leading end of the bone plate.

7. The method according to claim 1, wherein the first foot bone segment is a distal foot bone segment and the second foot bone segment is a proximal foot bone segment.

8. The method according to claim 1, wherein the first foot bone segment is a phalanges bone and the second foot bone segment is a metatarsal bone.

9. The method according to claim 1, wherein the first foot bone segment is a metatarsal bone and the second foot bone segment is a cuneiform bone.

10. A method, comprising:

forming a first incision near a first bone segment on a first side of a joint;

forming a second incision near a second bone segment on a second side of the joint;

inserting a leading end of a bone plate into the first incision until the leading end is located adjacent the first bone segment, wherein the leading end includes a first through-hole;

positioning the bone plate along the first bone segment and the second bone segment so that the bone plate spans the joint, with the leading end located on the first side of the joint, a trailing end of the bone plate with a second through-hole located on the second side of the joint, such that, the first through-hole and the second through-hole are each offset with respect to an axis that extends across and is perpendicular to the joint;

implanting a first bone anchor through the second incision into the first through-hole at the leading end of the bone plate and into the first bone segment; and implanting a second bone anchor through the first incision into the second through-hole of the trailing end of the bone plate and into the second bone segment.

11. The method according to claim 10, further comprising coupling one or more drill guides to a bone plate at one or more second through-holes, respectively, at the trailing end of the bone plate.

12. The method according to claim 11, wherein coupling the one or more drill guides to the bone plate includes threadably coupling the one or more drill guides to the one or more second through-holes, respectively, at the trailing end of the bone plate.

13. The method according to claim 12, further comprising, before implanting the one or more first bone anchors into the one or more through-holes at the trailing end of the bone plate, removing the one or more drill guides from the trailing end of the bone plate.

14. The method according to claim 10, wherein positioning the bone plate in the first incision so that the bone plate spans the first bone segment and the second bone segment further comprises positioning the bone plate so that a leading end is adjacent the second bone segment, the trailing end is adjacent the first bone segment and a central bridge of the bone plate spans the joint and the first and second bone segments, wherein the leading end and trailing end are angularly offset with respect to the central bridge.

15. The method according to claim 10, further comprising implanting one or more crossing anchors inferior to the bone plate and between shafts of the one or more first bone anchors and the one or more second bone anchors.

16. The method according to claim 15, wherein implanting the one or more crossing anchors occurs after implanting the second bone anchor into the second through-hole at the trailing end of the bone plate.

17. The method according to claim 16, wherein the first bone anchor includes two first bone anchors, the second bone anchor includes one two bone anchors.

18. The method according to claim 10, wherein the first bone segment is one or more first foot bones and the second bone segment is one or more second foot bones.

19. A method, comprising:

inserting a leading end of a bone plate into an incision and relative to a tendon and a first bone until the leading end is located adjacent a first bone segment of the first bone;

positioning the bone plate across the first bone segment and a second bone segment of the bone so that the bone plate is positioned relative to the tendon, the leading end having a first through-hole located on a first side of the tendon and a trailing end of the bone plate having a second through-hole located on a second side of the tendon;

fixing a first bone anchor into the first through-hole at the leading end of the bone plate and into the first bone segment of the first bone on the first side of the tendon; and fixing a second bone anchor into the second through-hole of the trailing end of the bone plate and into the second bone segment of the second bone on the second side of the tendon, such that, the first bone anchor and the second bone anchor are offset with respect to an axis that extends along the first and second bone segments and the bone plate is beneath the tendon.

20. The method according to claim 19, wherein the first bone segment and second bone segment is separated by a joint.

21. The method according to claim 19, further comprising implanting a crossing anchor across the first and second bone segments so that the crossing anchor does not interfere with the one or more first bone anchors and the one or more second bone anchors.

22. The method according to claim 21, further comprising coupling a targeting instrument to the bone plate before inserting the leading end of a bone plate into the incision.

23. A method, comprising:

inserting a leading end of a bone plate into an incision above a bone until the leading end is located adjacent to a first bone segment of the bone;

positioning the bone plate across a joint of the bone so that bone plate spans the first bone segment and a second bone segment, wherein the leading end is located on a first side of the joint, and a trailing end of the bone plate is located on a second side of the joint opposite the first side of the joint so that the leading end and the trailing end are angularly offset with respect to an axis that extends across the joint;

fixing one or more first bone anchors into one or more through-holes at the leading end of the bone plate and into the first bone segment of the bone;

fixing one or more second bone anchors into one or more through-holes of the trailing end of the bone plate and into the second bone segment of the bone; and implanting a crossing anchor across the first and second bone segments inferior to the bone plate and between shafts of the one or more first bone anchors and the one or more second bone anchors, so that the crossing anchor does not interfere with the one or more first bone anchors and the one or more second bone anchors.

24. The method according to claim 23, wherein the first bone segment and second bone segment is separated by a joint.

25. The method according to claim 23, before inserting the inserting the leading end of the bone plate into the incision, coupling one or more drill guides to the one or more through-holes located at the trailing end of the bone plate.

26. The method according to claim 25, wherein coupling the one or more drill guides to the bone plate includes threadably coupling the one or more drill guides to the one or more through-holes at the trailing end of the bone plate.

27. The method according to claim 26, further comprising, before implanting the one or more first bone anchors into the one or more through-holes at the trailing end of the bone plate, removing the one or more drill guides from the trailing end of the bone plate.

* * * * *